US010563190B2

(12) United States Patent
Royer

(10) Patent No.: US 10,563,190 B2
(45) Date of Patent: Feb. 18, 2020

(54) METHODS FOR PRODUCING ABIENOL

(71) Applicant: DSM IP ASSETS B.V., Heerlen (NL)

(72) Inventor: John Royer, Lexington, MA (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 15/534,681

(22) PCT Filed: Dec. 3, 2015

(86) PCT No.: PCT/US2015/063656
§ 371 (c)(1),
(2) Date: Jun. 9, 2017

(87) PCT Pub. No.: WO2016/094178
PCT Pub. Date: Jun. 16, 2016

(65) Prior Publication Data

US 2017/0362583 A1 Dec. 21, 2017

Related U.S. Application Data

(60) Provisional application No. 62/089,511, filed on Dec. 9, 2014.

(51) Int. Cl.

| | |
|---|---|
| ***C12N 9/88*** | (2006.01) |
| ***C07C 13/38*** | (2006.01) |
| ***C12N 15/52*** | (2006.01) |
| ***C12N 15/70*** | (2006.01) |
| ***C12N 15/81*** | (2006.01) |

(52) U.S. Cl.
CPC ................ *C12N 9/88* (2013.01); *C07C 13/38* (2013.01); *C12N 15/52* (2013.01); *C12N 15/70* (2013.01); *C12N 15/81* (2013.01); *C12Y 205/01029* (2013.01); *C12Y 402/0314* (2015.07); *C07C 2602/18* (2017.05)

(58) Field of Classification Search
None
See application file for complete search history.

(56) References Cited

U.S. PATENT DOCUMENTS 7,851,199 B2 12/2010 Bailey et al.
2013/0224809 A1 8/2013 Bohlmann et al.

FOREIGN PATENT DOCUMENTS

WO 2008/007031 1/2008
WO WO 2008/007031 1/2008
WO 2016/172282 10/2016
WO WO 2016/172282 A1 10/2016

OTHER PUBLICATIONS

International Search Report for PCT/US2015/063656, dated Feb. 19, 2016, 3 pages.

Written Opinion of the ISA for PCT/US2015/063656, dated Feb. 19, 2016, 9 pages.

Barrero et al, "Synthesis of *Ambrox*® from (−)-sclareol and (+)-cis-abienol," Tetrahedron vol. 49, No. 45, pp. 10405-10412, UK, 1993.

Gordon et al, "Risk Factors for and Treatment of Ketosis in Lactating Dairy Cattle," University of Guelph, Ontario, CA, Aug. 2013.

Needleman et al, "A General Method Applicable to the Search for Similarities in the Amino Acid Sequence of Two Proteins," *J.Mol. Biol.* (1970) 48, 443-453.

Rice et al, "EMBOSS: The European Molecular Biology Open Software Suite," TIG Jun. 2000, vol. 16, No. 6.

Sallud et al. "Characterization of Two Genes for the Biosynthesis of the Labdane Diterpene Z-abienol in Tobacco (*Nicotiana tabacurn*) Glandular Trichomes," *GenBank*, (Oct. 2012).

Caniard et al. "Discovery and Functional Characterization of Two Diterpene Synthases for Sclareol Biosynthesis in *Salvia sclarea* (L.) and their Relevance for Perfume Manufacture," GenBank, (Oct. 2012).

Sambrook, "Molecular Cloning—A Laboratory Manual" ($2^{nd}$ ed.), Cold Spring Harbo Laboratory Press, pp. xi-xxxviii *Contents* (1989).

Schalk et al, "Toward a Biosynthetic Route to Sclareol and Amber Odorants," *J. Am. Chem. Soc.* 2012, 134, 18900-18903.

Caniard et al., "Discovery and functional characterization of two diterpene synthases for sclareol biosynthesis in *Salvia sclarea* (L.) and their relevance for perfume manufacture," BMC Plant Biology, vol. 12:119; pp. 1-13 (2012).

Zerbe et al., "Bifunctional cis-Abienol Synthase from Abies balsamea Discovered by Transcriptome Sequencing and its Implications for Diterpenoid Fragrance Production," The Journal of Biological Chemistry, vol. 287:15 pgs. 12121-12131; (2012).

Ausubel, et al., "Current Protocols in Molecular Biology," Table of Contents, pp. 1-25 (2003).

Barrero et al., "Synthesis of Ambrox® from (−)-sclareol and (+)-cis-abienol," Tetrahedron, vol. 49:45; pp. 10405-10412; (1993).

Gordon et al., "Risk Factors for and Treatment of Ketosis in Lactating Dairy Cattle," A Thesis Presented to the University of Guelph, pp. 1-174 (2013).

Needleman et al., "A General Method Applicable to the Search for Similarities in the Amino Acid Sequence of Two Proteins," J. Mol. Biol., vol. 48; pp. 443-453 (1970).

Rice et al., "EMBOSS: The European Molecular Biology Open Software Suite," Resource Internet, vol. 16, No. 6, pp. 276-277 (2000).

Sallaud et al., "Characterization of two genes for the biosynthesis for the labdane diterpene Z-abienol in tobacco (*Nicotiana tabacum*) glandular trichomes," The Plant Journal, vol. 72; pp. 1-17 (2012).

Sambrook, "Molecular Cloning," A Laboratory Manual, second edition, table of contents (1989).

(Continued)

*Primary Examiner* — Suzanne M Noakes
(74) *Attorney, Agent, or Firm* — Nixon & Vanderhye P.C.

(57) ABSTRACT

The present disclosure relates to a novel method, expression vectors, and host cells for producing abienol by converting geranylgeranyl diphosphate (GGPP) to abienol in the presence of a combination of a class II diterpene synthase and a bifunctional class I/II abienol synthase.

11 Claims, 5 Drawing Sheets

Specification includes a Sequence Listing.

(56) References Cited

OTHER PUBLICATIONS

Schalk et al., "Toward a Biosynthetic Route to Sclareol and Amber Odorants," Journal of the American Chemical Society, vol. 134, pp. 18900-18903 (2012).
Unknown; GenBank CCD33018.1, 8-hydroxy-copalyl diphosphate synthase [Nicotiana tabacum]; (2012).
Unknown; GenBank AEL99953.1, diterpene synthase TPS4 [Abies balsamea]; (2012).
Unknown; GenBank AFU61897.1, labd-13-en-8-ol diphosphate synthase [Salvia sclarea]; (2012).

I (-)-Sclareol

Ambrox
(Ambroxan)

II (+)-cis-abienol

Geranylgeranyl diphosphate

Labdenediol diphosphate

Sclareol (Clary Sage)

Abienol (Tobacco)

SEQUENCE LISTING

<160> NUMBER OF SEQ ID NOS: 9

<210> SEQ ID NO 1
<211> LENGTH: 802
<212> TYPE: PRT
<213> ORGANISM: Nicotiana tabacum

<400> SEQUENCE: 1

Met Gln Val Ile Ile Thr Ser Ser His Arg Phe Phe Cys His His Leu
1 5 10 15

His Gln Leu Lys Ser Pro Thr Ser Leu Ser Ala Gln Lys Ala Glu Phe
20 25 30

Lys Lys His Gly Pro Arg Asn Trp Leu Phe Gln Thr Glu Gly Ser Leu
35 40 45

Leu Tyr Lys Pro Val Arg Leu Asn Cys Ala Thr Ser Asp Ala Ser Tyr
50 55 60

Leu Gly Asn Val Asn Glu Tyr Leu Glu Ser Asp His Ser Lys Asn Ser
65 70 75 80

Glu Glu Lys Asp Ile Gln Val Ser Arg Thr Ile Gln Met Lys Gly Leu
85 90 95

Thr Glu Glu Ile Lys His Met Leu Asn Ser Met Glu Asp Gly Arg Leu
100 105 110

Asn Val Leu Ala Tyr Asp Thr Ala Trp Val Ser Phe Ile Pro Asn Thr
115 120 125

Thr Asn Asn Gly Asn Asp Gln Arg Pro Met Phe Pro Ser Cys Leu Gln
130 135 140

Trp Ile Ile Asp Asn Gln Leu Ser Asp Gly Ser Trp Gly Glu Glu Ile
145 150 155 160

Val Phe Cys Ile Tyr Asp Arg Leu Leu Asn Thr Leu Val Cys Val Ile
165 170 175

Ala Leu Thr Leu Trp Asn Thr Cys Leu His Lys Arg Asn Lys Gly Val
180 185 190

Met Phe Ile Lys Glu Asn Leu Ser Lys Leu Glu Thr Gly Glu Val Glu

-continued

```
        195                 200                 205

Asn Met Thr Ser Gly Phe Glu Leu Val Phe Pro Thr Leu Leu Glu Lys
    210                 215                 220

Ala Gln Gln Leu Asp Ile Asp Ile Pro Tyr Asp Ala Pro Val Leu Lys
225                 230                 235                 240

Asp Ile Tyr Ala Arg Arg Glu Val Lys Leu Thr Arg Ile Pro Lys Asp
                245                 250                 255

Val Ile His Thr Ile Pro Thr Thr Val Leu Phe Ser Leu Glu Gly Leu
            260                 265                 270

Arg Asp Asp Leu Asp Trp Gln Arg Leu Leu Lys Leu Gln Met Pro Asp
        275                 280                 285

Gly Ser Phe Leu Ile Ser Pro Ala Ser Thr Ala Phe Ala Phe Met Glu
    290                 295                 300

Thr Asn Asp Glu Lys Cys Leu Ala Tyr Leu Gln Asn Val Val Glu Lys
305                 310                 315                 320

Ser Asn Gly Gly Ala Arg Gln Tyr Pro Phe Asp Leu Val Thr Arg Leu
                325                 330                 335

Trp Ala Ile Asp Arg Leu Gln Arg Leu Gly Ile Ser Tyr Tyr Phe Ala
            340                 345                 350

Glu Glu Phe Lys Glu Leu Leu Asn His Val Phe Arg Tyr Trp Asp Glu
        355                 360                 365

Glu Asn Gly Ile Phe Ser Gly Arg Asn Ser Asn Val Ser Asp Val Asp
    370                 375                 380

Asp Thr Cys Met Ala Ile Arg Leu Leu Arg Leu His Gly Tyr Asp Val
385                 390                 395                 400

Ser Pro Asp Ala Leu Asn Asn Phe Lys Asp Gly Asp Gln Phe Val Cys
                405                 410                 415

Phe Arg Gly Glu Val Asp Gly Ser Pro Thr His Met Phe Asn Leu Tyr
            420                 425                 430

Arg Cys Ser Gln Val Leu Phe Pro Gly Glu Lys Ile Leu Glu Glu Ala
        435                 440                 445

Lys Asn Phe Thr Tyr Asn Phe Leu Gln Gln Cys Leu Ala Asn Asn Arg
    450                 455                 460

Cys Leu Asp Lys Trp Val Ile Ala Lys Asp Ile Pro Gly Glu Ile Trp
465                 470                 475                 480

Tyr Ala Leu Glu Phe Pro Trp Tyr Ala Ser Leu Pro Arg Val Glu Ala
                485                 490                 495

Arg Tyr Tyr Ile Glu Gln Tyr Gly Gly Ala Asp Asp Ile Trp Ile Gly
            500                 505                 510

Lys Thr Leu Tyr Arg Met Pro Asp Val Asn Asn Asn Val Tyr Leu Gln
        515                 520                 525

Ala Ala Lys Leu Asp Tyr Asn Arg Cys Gln Ser Gln His Arg Phe Glu
    530                 535                 540

Trp Leu Ile Met Gln Glu Trp Phe Glu Lys Cys Asn Phe Gln Gln Phe
545                 550                 555                 560

Gly Ile Ser Lys Lys Tyr Leu Leu Val Ser Tyr Phe Leu Ala Ala Ala
                565                 570                 575

Ser Ile Phe Glu Val Glu Lys Ser Arg Glu Arg Leu Ala Trp Ala Lys
            580                 585                 590

Ser Arg Ile Ile Cys Lys Met Ile Thr Ser Tyr Tyr Asn Asp Glu Ala
        595                 600                 605

Thr Thr Trp Thr Thr Arg Asn Ser Leu Leu Met Glu Phe Lys Val Ser
    610                 615                 620
```

-continued

```
His Asp Pro Thr Arg Lys Asn Gly Asn Glu Thr Lys Glu Ile Leu Val
625                 630                 635                 640

Leu Lys Asn Leu Arg Gln Phe Leu Arg Gln Leu Ser Glu Glu Thr Phe
                645                 650                 655

Glu Asp Leu Gly Lys Asp Ile His His Gln Leu Gln Asn Ala Trp Glu
            660                 665                 670

Thr Trp Leu Val Phe Leu Arg Glu Glu Lys Asn Ala Cys Gln Glu Glu
        675                 680                 685

Thr Glu Leu Leu Val Arg Thr Ile Asn Leu Ser Gly Gly Tyr Met Thr
    690                 695                 700

His Asp Glu Ile Leu Phe Asp Ala Asp Tyr Glu Asn Leu Ser Asn Leu
705                 710                 715                 720

Thr Asn Lys Val Cys Gly Lys Leu Asn Glu Leu Gln Asn Asp Lys Val
                725                 730                 735

Thr Gly Gly Ser Lys Asn Thr Asn Ile Glu Leu Asp Met Gln Ala Leu
            740                 745                 750

Val Lys Leu Val Phe Gly Asn Thr Ser Ser Asn Ile Asn Gln Asp Ile
        755                 760                 765

Lys Gln Thr Phe Phe Ala Val Val Lys Thr Phe Tyr Tyr Ser Ala His
    770                 775                 780

Val Ser Glu Glu Ile Met Asn Phe His Ile Ser Lys Val Leu Phe Gln
785                 790                 795                 800

Gln Val


<210> SEQ ID NO 2
<211> LENGTH: 780
<212> TYPE: PRT
<213> ORGANISM: Salvia sclarea

<400> SEQUENCE: 2

Met Thr Ser Val Asn Leu Ser Arg Ala Pro Ala Ala Ile Ile Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Phe Thr Leu Ser Cys Gln Ile Arg Pro
        35                  40                  45

Lys Gln Leu Ser Gln Ile Ala Glu Leu Arg Val Thr Ser Leu Asp Ala
    50                  55                  60

Ser Gln Ala Ser Glu Lys Asp Ile Ser Leu Val Gln Thr Pro His Lys
65                  70                  75                  80

Val Glu Val Asn Glu Lys Ile Glu Glu Ser Ile Glu Tyr Val Gln Asn
                85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His His Gln Leu Ala Asp
    130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu Gln Ser Asp
                165                 170                 175

Ile Ile Glu Lys Gly Val Thr Tyr Ile Lys Glu Asn Val His Lys Leu
            180                 185                 190
```

```
Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Gly Leu Pro
    210                 215                 220

Tyr Asp His Pro Leu Ile Lys Glu Ile Ala Asp Thr Lys Lys Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
            340                 345                 350

Ile Glu Ser Val Trp Glu Glu Thr Gly Val Phe Ser Gly Arg Tyr Thr
        355                 360                 365

Lys Phe Ser Asp Ile Asp Asp Thr Ser Met Gly Val Arg Leu Leu Lys
    370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
            420                 425                 430

Glu Glu Val Phe Glu Glu Ala Thr Lys Phe Ala Phe Asn Phe Leu Gln
        435                 440                 445

Glu Met Leu Val Lys Asp Arg Leu Gln Glu Arg Trp Val Ile Ser Asp
    450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
        515                 520                 525

Gln Thr Gln His Gln Leu Glu Trp Ile His Met Gln Glu Trp Tyr Asp
    530                 535                 540

Arg Cys Ser Leu Ser Glu Phe Gly Ile Ser Lys Arg Glu Leu Leu Arg
545                 550                 555                 560

Ser Tyr Phe Leu Ala Ala Ala Thr Ile Phe Glu Pro Glu Arg Thr Gln
                565                 570                 575

Glu Arg Leu Leu Leu Ala Lys Thr Arg Ile Leu Ser Lys Met Ile Thr
            580                 585                 590

Ser Phe Val Asn Ile Ser Gly Thr Thr Leu Ser Leu Asp Tyr Asn Phe
        595                 600                 605
```

```
Asn Gly Leu Asp Glu Ile Ile Ser Ser Ala Asn Glu Asp Gln Gly Leu
    610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Glu Gly Ser Gly Gly Glu Asp Ala Val Leu Leu
            660                 665                 670

Ala Asn Thr Leu Asn Ile Cys Ala Gly Leu Asn Glu Asp Val Leu Ser
        675                 680                 685

Asn Asn Glu Tyr Thr Ala Leu Ser Thr Leu Thr Asn Lys Ile Cys Asn
    690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735

Leu Val Leu Gln Glu Asn Gly Gly Ala Val Asp Arg Asn Ile Arg His
            740                 745                 750

Thr Phe Leu Ser Val Phe Lys Thr Phe Tyr Tyr Asp Ala Tyr His Asp
        755                 760                 765

Asp Glu Thr Thr Asp Leu His Ile Phe Lys Val Leu
    770                 775                 780


<210> SEQ ID NO 3
<211> LENGTH: 867
<212> TYPE: PRT
<213> ORGANISM: Abies balsamea

<400> SEQUENCE: 3

Met Ala Leu Pro Val Tyr Ser Leu Lys Ser His Ile Pro Ile Thr Thr
1               5                   10                  15

Ile Ala Ser Ala Lys Met Asn Tyr Thr Pro Asn Lys Gly Met Ile Thr
            20                  25                  30

Ala Asn Gly Arg Ser Arg Arg Ile Arg Leu Ser Pro Asn Lys Ile Val
        35                  40                  45

Ala Cys Ala Gly Glu Ala Asp Arg Thr Phe Pro Ser Gln Ser Leu Glu
    50                  55                  60

Lys Thr Ala Leu Phe Pro Asp Gln Phe Ser Glu Lys Asn Gly Thr Pro
65                  70                  75                  80

Ser Asn Phe Thr Pro Pro Asn Arg Glu Phe Pro Pro Ser Phe Trp Asn
                85                  90                  95

Asn Asp Ile Ile Asn Ser Ile Thr Ala Ser His Lys Val Gln Thr Gly
            100                 105                 110

Asp Arg Lys Arg Ile Gln Thr Leu Ile Ser Glu Ile Lys Asn Val Phe
        115                 120                 125

Asn Ser Met Gly Asp Gly Glu Thr Ser Pro Ser Ala Tyr Asp Thr Ala
    130                 135                 140

Trp Val Ala Arg Ile Pro Ala Val Asp Gly Ser Glu Gln Pro Gln Phe
145                 150                 155                 160

Pro Gln Thr Leu Glu Trp Ile Leu Gln Asn Gln Leu Lys Asp Gly Ser
                165                 170                 175

Trp Gly Glu Glu Phe Tyr Phe Leu Ala Tyr Asp Arg Leu Leu Ala Thr
            180                 185                 190

Leu Ala Cys Ile Ile Thr Leu Thr Ile Trp Arg Thr Gly Asn Val Gln
        195                 200                 205
```

-continued

```
Leu His Lys Gly Ile Glu Phe Phe Arg Lys Gln Val Val Arg Met Asp
    210                 215                 220

Asp Glu Ala Asp Asn His Arg Pro Ser Gly Phe Glu Ile Val Phe Pro
225                 230                 235                 240

Ala Met Leu Asn Glu Ala Lys Ser Leu Gly Leu Asp Leu Pro Tyr Glu
                245                 250                 255

Leu Pro Phe Ile Glu Gln Met Val Lys Lys Arg Glu Ala Lys Leu Lys
            260                 265                 270

Met Ile Thr Thr Asn Val Leu Tyr Thr Ile Gln Thr Thr Leu Leu Tyr
        275                 280                 285

Ser Leu Glu Gly Leu His Glu Ile Val Asp Phe Asp Lys Ile Ile Lys
    290                 295                 300

Leu Gln Ser Lys Asp Gly Ser Phe Leu Gly Ser Pro Ala Ser Thr Ala
305                 310                 315                 320

Ala Val Phe Met Gln Thr Gly Asn Thr Lys Cys Leu Glu Phe Leu Glu
                325                 330                 335

Phe Val Leu Arg Lys Phe Arg Asn His Val Pro Ser Asp Tyr Pro Leu
            340                 345                 350

Asp Leu Phe Glu Arg Leu Trp Val Val Asp Thr Val Glu Arg Leu Gly
        355                 360                 365

Ile Asp Arg His Phe Lys Lys Glu Ile Lys Asp Ala Leu Asp Tyr Val
    370                 375                 380

Tyr Ser Cys Trp Asp Glu Arg Gly Ile Gly Trp Ala Lys Asp Ser Pro
385                 390                 395                 400

Ile Ala Asp Ile Asp Asp Thr Ala Met Gly Leu Arg Ile Leu Arg Leu
                405                 410                 415

His Gly Tyr Asn Val Ser Pro Asp Val Leu Lys Thr Phe Lys Asp Glu
            420                 425                 430

Asn Gly Glu Phe Phe Cys Phe Met Gly Gln Thr Gln Arg Gly Val Thr
        435                 440                 445

Asp Met Leu Asn Val Tyr Arg Cys Ser Gln Val Ala Phe Pro Gly Glu
    450                 455                 460

Thr Ile Met Glu Glu Ala Lys Leu Cys Thr Glu Arg Tyr Leu Arg Asn
465                 470                 475                 480

Ala Leu Glu Asn Ala Asp Ala Phe Asp Lys Trp Ala Ile Lys Lys Asn
                485                 490                 495

Ile Arg Gly Glu Val Glu Tyr Ala Leu Lys Tyr Pro Trp His Arg Ser
            500                 505                 510

Met Pro Arg Leu Glu Val Arg Ser Tyr Ile Gly Asn Tyr Gly Pro Asn
        515                 520                 525

Asp Val Trp Leu Gly Lys Ser Leu Tyr Met Met Pro Tyr Ile Ser Asn
    530                 535                 540

Glu Lys Tyr Leu Glu Leu Ala Lys Leu Asp Phe Asn Ser Val Gln Ser
545                 550                 555                 560

Leu His Gln Glu Glu Ile Arg Glu Leu Val Arg Trp Cys Lys Ser Ser
                565                 570                 575

Gly Phe Thr Glu Leu Lys Phe Thr Arg Asp Arg Val Val Glu Thr Tyr
            580                 585                 590

Phe Ala Val Ala Ser Ser Met Phe Glu Pro Glu Phe Ser Thr Cys Arg
        595                 600                 605

Ala Val Tyr Thr Lys Ile Ser Val Leu Leu Val Ile Leu Asp Asp Leu
    610                 615                 620
```

```
Tyr Asp Gly Tyr Gly Ser Pro Asp Glu Ile Lys Leu Phe Ser Glu Ala
625                 630                 635                 640

Val Lys Arg Trp Asp Leu Ser Leu Leu Glu Gln Met Pro Asp His Met
                645                 650                 655

Lys Ile Cys Phe Leu Gly Leu Tyr Asn Thr Val Asn Glu Val Ala Glu
            660                 665                 670

Glu Gly Arg Lys Thr Gln Gly His Asp Val Leu Gly Tyr Ile Arg Asn
        675                 680                 685

Leu Trp Glu Ile Gln Leu Ala Ala Phe Thr Arg Glu Ala Glu Trp Ser
    690                 695                 700

Gln Gly Lys Tyr Val Pro Ser Phe Asp Glu Tyr Ile Glu Asn Ala Gln
705                 710                 715                 720

Val Ser Ile Gly Val Ala Thr Ile Leu Leu Ile Thr Ile Leu Phe Thr
                725                 730                 735

Glu Glu Asp Asp Ile Leu Ser His Ile Asp Tyr Gly Ser Lys Phe Leu
            740                 745                 750

Arg Leu Ala Ser Leu Thr Ala Arg Leu Ala Asn Asp Ile Lys Thr Tyr
        755                 760                 765

Gln Glu Glu Arg Ala His Gly Glu Val Val Ser Ala Ile Gln Cys Tyr
    770                 775                 780

Met Lys Asp Arg Pro Glu Ile Thr Glu Glu Glu Ala Leu Lys Tyr Val
785                 790                 795                 800

Tyr Gly Arg Met Val Asn Asp Leu Ala Glu Leu Asn Ser Glu Tyr Leu
                805                 810                 815

Lys Ser Asn Glu Met Pro Gln Asn Cys Lys Arg Leu Val Phe Asp Thr
            820                 825                 830

Ala Arg Val Ala Gln Leu Phe Thr Met Glu Gly Asp Gly Leu Thr Tyr
        835                 840                 845

Ser Asp Thr Met Glu Ile Lys Glu His Ile Lys Lys Cys Leu Phe Glu
    850                 855                 860

Pro Ala Thr
865


<210> SEQ ID NO 4
<211> LENGTH: 792
<212> TYPE: PRT
<213> ORGANISM: Nicotiana tabacum

<400> SEQUENCE: 4

Met Val Leu Gly Leu Arg Ser Lys Ile Ile Pro Leu Pro Asp His Lys
1               5                   10                  15

Leu Gly Asn Ile Lys Leu Gly Ser Val Thr Asn Ala Ile Cys His Arg
            20                  25                  30

Pro Cys Arg Val Arg Cys Ser His Ser Thr Ala Ser Ser Met Glu Glu
        35                  40                  45

Ala Lys Glu Arg Ile Arg Glu Thr Phe Gly Lys Ile Glu Leu Ser Pro
    50                  55                  60

Ser Ser Tyr Asp Thr Ala Trp Val Ala Met Val Pro Ser Arg Tyr Ser
65                  70                  75                  80

Met Asn Gln Pro Cys Phe Pro Gln Cys Leu Asp Trp Ile Leu Glu Asn
                85                  90                  95

Gln Arg Glu Asp Gly Ser Trp Gly Leu Asn Pro Ser His Pro Leu Leu
            100                 105                 110

Val Lys Asp Ser Leu Ser Ser Thr Leu Ala Ser Leu Leu Ala Leu Arg
        115                 120                 125
```

-continued

```
Lys Trp Arg Ile Gly Asp Asn Gln Val Gln Arg Gly Leu Gly Phe Ile
    130                 135                 140

Glu Thr His Gly Trp Ala Val Asp Asn Lys Asp Gln Ile Ser Pro Leu
145                 150                 155                 160

Gly Phe Glu Ile Ile Phe Pro Cys Met Ile Asn Tyr Ala Glu Lys Leu
                165                 170                 175

Asn Leu Asp Leu Pro Leu Asp Pro Asn Leu Val Asn Met Met Leu Cys
            180                 185                 190

Glu Arg Glu Leu Thr Ile Glu Arg Ala Leu Lys Asn Glu Phe Glu Gly
        195                 200                 205

Asn Met Ala Asn Val Glu Tyr Phe Ala Glu Gly Leu Gly Glu Leu Cys
    210                 215                 220

His Trp Lys Glu Met Met Leu Arg Gln Arg His Asn Gly Ser Leu Phe
225                 230                 235                 240

Asp Ser Pro Ala Thr Thr Ala Ala Ala Leu Ile Tyr His Gln Tyr Asp
                245                 250                 255

Glu Lys Cys Phe Gly Tyr Leu Asn Ser Ile Leu Lys Leu His Asp Asn
            260                 265                 270

Trp Val Pro Thr Ile Cys Pro Thr Lys Ile His Ser Asn Leu Phe Leu
        275                 280                 285

Val Asp Ala Leu Gln Asn Leu Gly Val Asp Arg Tyr Phe Lys Thr Glu
    290                 295                 300

Val Lys Arg Val Leu Asp Glu Ile Tyr Arg Leu Trp Leu Glu Lys Asn
305                 310                 315                 320

Glu Glu Ile Phe Ser Asp Val Ala His Cys Ala Met Ala Phe Arg Leu
                325                 330                 335

Leu Arg Met Asn Asn Tyr Glu Val Ser Ser Glu Glu Leu Glu Gly Phe
            340                 345                 350

Val Asp Gln Glu His Phe Phe Thr Thr Ser Ser Gly Lys Leu Met Asn
        355                 360                 365

His Val Ala Ile Leu Glu Leu His Arg Ala Ser Gln Val Ala Ile His
    370                 375                 380

Glu Arg Lys Asp His Ile Leu Asp Lys Ile Ser Thr Trp Thr Arg Asn
385                 390                 395                 400

Phe Met Glu Gln Lys Leu Leu Asp Lys His Ile Pro Asp Arg Ser Lys
                405                 410                 415

Lys Glu Met Glu Phe Ala Met Arg Lys Phe Tyr Gly Thr Phe Asp Arg
            420                 425                 430

Val Glu Thr Arg Arg Tyr Ile Glu Ser Tyr Lys Met Asp Ser Phe Lys
        435                 440                 445

Ile Leu Lys Ala Ala Tyr Arg Ser Ser Gly Ile Asn Asn Ile Asp Leu
    450                 455                 460

Leu Lys Phe Ser Glu His Asp Phe Asn Leu Cys Gln Thr Arg His Lys
465                 470                 475                 480

Glu Glu Leu Gln Gln Met Lys Arg Trp Phe Thr Asp Cys Lys Leu Glu
                485                 490                 495

Gln Val Gly Leu Ser Gln Gln Tyr Leu Tyr Thr Ser Tyr Phe Ile Ile
            500                 505                 510

Ala Ala Ile Leu Phe Glu Pro Glu Tyr Ala Asp Ala Arg Leu Ala Tyr
        515                 520                 525

Ala Lys Tyr Ala Ile Ile Ile Thr Ala Val Asp Asp Phe Phe Asp Cys
    530                 535                 540
```

-continued

```
Phe Ile Cys Lys Glu Glu Leu Gln Asn Ile Ile Glu Leu Val Glu Arg
545                 550                 555                 560

Trp Glu Gly Tyr Ser Thr Val Gly Phe Arg Ser Glu Arg Val Arg Ile
                565                 570                 575

Phe Phe Leu Ala Leu Tyr Lys Met Val Glu Glu Ile Ala Ala Lys Ala
            580                 585                 590

Glu Thr Lys Gln Gly Arg Cys Val Lys Asp His Leu Ile Asn Leu Trp
        595                 600                 605

Ile Asp Met Leu Lys Cys Met Leu Val Glu Leu Asp Leu Trp Lys Ile
    610                 615                 620

Lys Ser Thr Thr Pro Ser Ile Glu Glu Tyr Leu Ser Val Ala Cys Val
625                 630                 635                 640

Thr Ile Gly Val Pro Cys Phe Val Leu Thr Ser Leu Tyr Leu Leu Gly
                645                 650                 655

Pro Lys Leu Ser Lys Asp Val Ile Glu Ser Ser Glu Val Ser Ala Leu
            660                 665                 670

Cys Asn Cys Thr Ala Ala Val Ala Arg Leu Ile Asn Asp Ile His Ser
        675                 680                 685

Tyr Lys Arg Glu Gln Ala Glu Ser Ser Thr Asn Met Val Ser Ile Leu
    690                 695                 700

Ile Thr Gln Ser Gln Gly Thr Ile Ser Glu Glu Glu Ala Ile Arg Gln
705                 710                 715                 720

Ile Lys Glu Met Met Glu Ser Lys Arg Arg Glu Leu Leu Gly Met Val
                725                 730                 735

Leu Gln Asn Lys Glu Ser Gln Leu Pro Gln Val Cys Lys Asp Leu Phe
            740                 745                 750

Trp Thr Thr Ile Asn Ala Ala Tyr Ser Ile His Thr His Gly Asp Gly
        755                 760                 765

Tyr Arg Phe Pro Glu Glu Phe Lys Asn His Ile Asn Asp Val Ile Tyr
    770                 775                 780

Lys Pro Leu Asn Gln Tyr Ser Pro
785                 790
```

<210> SEQ ID NO 5
<211> LENGTH: 2409
<212> TYPE: DNA
<213> ORGANISM: Yarrowia lipolytica

<400> SEQUENCE: 5

```
atgcaggtta ttattacctc ctctcaccga tttttctgcc accaccttca ccagctcaag     60

tcccctacct ccctttctgc tcagaaggct gagtttaaga agcacggccc ccgaaactgg    120

cttttccaga ctgagggctc tctcctttac aagcctgtcc gactcaactg tgctacttct    180

gatgcttctt accttggtaa cgtgaacgag taccttgagt ctgaccactc taagaactcc    240

gaggagaagg atattcaggt ttcccgaact atccagatga agggtcttac cgaggagatc    300

aagcacatgc ttaactctat ggaggacgga cgacttaacg tcctcgccta cgacactgct    360

tgggtttcct ttattcctaa cactaccaac aacggaaacg atcagcgacc tatgtttccc    420

tcttgtcttc agtggattat tgacaaccag ctttctgatg gttcttgggg agaggagatt    480

gttttctgca tttacgaccg actccttaac actctcgttt gtgttattgc tctcactctc    540

tggaacactt gccttcacaa gcgaaacaag ggtgtgatgt ttatcaagga gaacctttct    600

aagctggaga ctggtgaggt tgagaacatg acttctggtt ttgagcttgt ttttcccact    660

ctccttgaga aggcccagca gctcgatatt gacattccct acgatgctcc tgtcctgaag    720
```

```
gatatttacg ctcgacgaga ggttaagctc acccgaatcc ctaaggacgt tatccacact    780

attcccacta ccgttctctt ttctcttgag ggactccgag atgacctcga ctggcagcga    840

ctcctgaagc tccagatgcc tgacggttct ttcctgattt cccctgcttc cactgccttt    900

gctttcatgg agactaacga tgagaagtgt cttgcctacc ttcagaacgt tgttgagaag    960

tctaacggag gtgcccgaca gtaccccttc gaccttgtta ctcgactttg ggccattgat   1020

cgactccagc gactcggaat ctcttactac tttgccgagg agttcaagga gcttctcaac   1080

cacgtgttcc gatactggga cgaggagaac ggaattttct ctggacgaaa ctctaacgtt   1140

tctgatgttg atgacacttg catggctatc cgacttctcc gacttcacgg ttacgatgtt   1200

tcccctgacg cccttaacaa cttcaaggac ggcgaccagt tcgtttgctt ccgaggtgag   1260

gtggacggtt ctcctaccca catgtttaac ctctaccgat gttcccaggt tcttttcccc   1320

ggagagaaga ttcttgagga ggctaagaac ttcacttaca acttccttca gcagtgcctt   1380

gctaacaacc gatgcctcga caagtgggtc attgctaagg acatccccgg cgagatttgg   1440

tacgctcttg agtttccctg gtacgcctcc cttccccgag tggaggctcg atactacatt   1500

gagcagtacg gcggagctga cgatatttgg attggcaaga ctctctaccg aatgcccgat   1560

gtcaacaaca acgtttacct tcaggctgcc aagctcgatt acaaccgatg ccagtcccag   1620

caccgatttg agtggctgat tatgcaggag tggtttgaga agtgcaactt tcagcagttc   1680

ggaatttcca agaagtacct ccttgtttct tacttccttg ctgccgcttc tatttttgag   1740

gtcgagaagt cccgagagcg acttgcttgg gctaagtctc gaattatctg taagatgatt   1800

acttcttact acaacgatga ggccactacc tggaccactc gaaactctct ccttatggag   1860

tttaaggttt ctcacgaccc tacccgaaag aacggtaacg agactaagga gatccttgtt   1920

ctcaagaacc ttcgacagtt ccttcgacag ctttctgagg agactttcga ggaccttggc   1980

aaggacatcc accaccagct tcagaacgct tgggagactt ggcttgtttt ccttcgagag   2040

gagaagaacg cttgtcagga ggagactgag cttctcgtgc gaactattaa cctctctggc   2100

ggctacatga cccacgatga gattcttttc gatgccgact acgagaacct gtccaacctt   2160

accaacaagg tttgtggcaa gctcaacgag cttcagaacg acaaggtcac tggcggctct   2220

aagaacacca acattgagct tgacatgcag gctctcgtta agctggtttt tggtaacacc   2280

tcctctaaca tcaaccagga cattaagcag actttctttg ctgttgtcaa gaccttctac   2340

tactctgccc acgtttctga ggagattatg aactttcaca tttccaaggt gctctttcag   2400

caggtctaa                                                           2409
```

```
<210> SEQ ID NO 6
<211> LENGTH: 2358
<212> TYPE: DNA
<213> ORGANISM: Yarrowia lipolytica

<400> SEQUENCE: 6

atgacttctg ttaacctttc ccgagccccc gctgccatta tccgacgacg acttcagctt     60

cagcctgagt ttcacgccga gtgttcttgg ctgaagtctt cttccaagca cgccccccttc    120

accctttcct gccagattcg acctaagcag ctctcccaga ttgccgagct tcgagttact    180

tccctcgatg cttcccaggc ttccgagaag gacatttccc ttgttcagac tccccacaag    240

gttgaggtta acgagaagat cgaggagtct atcgagtacg tccagaacct tctcatgact    300

tccggcgacg gacgaatttc tgtgtccccc tacgacaccg ctgtgatcgc cctgattaag    360
```

```
gacctcaagg gtcgagatgc ccctcagttt ccctcttgtc ttgagtggat tgcccaccac    420

cagcttgctg atggctcttg gggcgacgag ttcttctgta tttacgaccg aatcctgaac    480

actctcgctt gtgtcgtcgc cctgaagtct tggaaccttc agtctgatat tattgagaag    540

ggtgtgacct acatcaagga gaacgtccac aagctcaagg gtgccaacgt tgagcaccga    600

actgccggat tcgagcttgt ggttcctacc tttatgcaga tggccactga ccttggcatt    660

cagggtcttc cctacgatca ccccctcatc aaggagattg ctgacactaa gaagcagcga    720

ctcaaggaga ttcccaagga tctcgtttac cagatgccta ccaaccttct ctactccctt    780

gagggactcg gcgaccttga gtgggagcga ctcctgaagc tccagtccgg caacggctcc    840

ttcctcactt cccccctcctc caccgccgcc gtccttatgc acaccaagga cgagaagtgt    900

ctgaagtaca tcgagaacgc cctcaagaac tgcgacggag gtgctcccca cacttaccct    960

gtcgatattt tctctcgact ttgggctatt gatcgacttc agcgacttgg tatttctcga   1020

ttcttccagc acgagatcaa gtacttcctc gatcacatcg agtccgtttg ggaggagacc   1080

ggagttttct ctggacgata cactaagttt tctgatattg atgacacctc tatgggcgtt   1140

cgacttctca agatgcacgg atacgacgtc gatcccaacg ttctcaagca cttcaagcag   1200

caggatggta agttttcctg ctacattggt cagtctgtcg agtctgcctc tcctatgtac   1260

aacctttacc gagccgccca gcttcgattc cctggtgagg aggtttttga ggaggccact   1320

aagtttgcct ttaacttcct tcaggagatg cttgtcaagg atcgacttca ggagcgatgg   1380

gtgatttccg accacctttt cgatgagatt aagctgggcc tcaagatgcc ttggtacgcc   1440

acccttcccc gagtcgaggc cgcttactac ctcgatcact acgctggttc tggtgatgtt   1500

tggattggca agtctttcta ccgaatgcct gagatttcca acgataccta caaggagctt   1560

gccattctcg atttcaaccg atgccagact cagcaccagc ttgagtggat tcacatgcag   1620

gagtggtacg accgatgctc tctttccgag ttcggcattt ccaagcgaga gcttctccga   1680

tcttactttc tcgccgccgc taccattttc gagcctgagc gaactcagga gcgacttctc   1740

cttgccaaga cccgaatcct gtctaagatg attacttctt ttgtcaacat ttccggtact   1800

accctttctc tcgactacaa cttcaacggc ctcgatgaga ttatctcctc tgccaacgag   1860

gatcagggtc tggctggtac tctcctggct accttccacc agcttctcga cggattcgat   1920

atttacactc tccaccagct caagcacgtt tggtcccagt ggttcatgaa ggtgcagcag   1980

ggagagggtt ctggcggcga ggacgccgtg ctccttgcca acaccctcaa catctgcgcc   2040

ggcctcaacg aggacgtgct ctccaacaac gagtacactg ctctgtccac cctcaccaac   2100

aagatttgca accgactcgc ccagatccag gacaacaaga ttctccaggt tgtggacggc   2160

tccatcaagg ataaggagct tgagcaggat atgcaggccc ttgtcaagct cgtccttcag   2220

gagaacggcg gagccgttga ccgaaacatc cgacacacct tcctttccgt tttcaagact   2280

ttctactacg atgcctacca cgacgatgag actaccgacc ttcacatctt caaggttctc   2340

tttcgacccg ttgtgtaa                                                 2358
```

<210> SEQ ID NO 7
<211> LENGTH: 2604
<212> TYPE: DNA
<213> ORGANISM: Yarrowia lipolytica

<400> SEQUENCE: 7

```
atggccctgc ccgtttactc tctcaagtcc cacattccca tcactaccat cgcctctgct     60

aagatgaact acaccccccaa caagggtatg attaccgcca acggacgatc tcgacgaatc    120
```

-continued

```
cgactttctc ccaacaagat cgttgcttgt gctggtgagg ctgatcgaac tttcccctct    180
cagtcccttg agaagaccgc tctctttccc gatcagtttt ctgagaagaa cggtactccc    240
tctaacttca ctccccccaa ccgagagttt ccccccctctt tttggaacaa cgatattatc    300
aactctatta ctgcttctca caaggttcag actggcgacc gaaagcgaat ccagactctc    360
atttctgaga ttaagaacgt ctttaactct atgggcgatg gtgagacttc tccctctgct    420
tacgacaccg cttgggttgc tcgaatcccc gccgttgatg gctctgagca gccccagttt    480
ccccagactc ttgagtggat tcttcagaac cagctcaagg acggttcttg ggtgaggag    540
ttctacttcc ttgcttacga ccgacttctc gctacccttg cctgcattat taccctcacc    600
atttggcgaa ctggcaacgt tcagcttcac aagggcattg agttcttccg aaagcaggtt    660
gttcgaatgg acgatgaggc tgataaccac cgaccctctg gttttgagat tgtctttccc    720
gctatgctta acgaggctaa gtcccttggt cttgacctgc cctacgagct tcccttcatt    780
gagcagatgg ttaagaagcg agaggccaag ctcaagatga ttaccaccaa cgtcctgtac    840
accattcaga ctaccctcct ttactctctg gagggccttc acgagattgt tgacttcgat    900
aagattatca agctccagtc caaggacggt tctttcctcg gctcccccgc ttctactgcc    960
gctgttttca tgcagactgg taacactaag tgccttgagt tccttgagtt cgttctccga   1020
aagtttcgaa accacgtgcc ctctgactac cccctcgatc tctttgagcg actttgggtc   1080
gttgacactg ttgagcgact tggcattgat cgacacttca agaaggagat caaggacgct   1140
cttgactacg tgtactcttg ttgggacgag cgaggcattg gctgggccaa ggactctccc   1200
atcgccgata ttgatgacac tgctatgggc cttcgaatcc ttcgactgca cggatacaac   1260
gtttcccccg atgttctcaa gactttcaag gacgagaacg gagagttctt ttgcttcatg   1320
ggtcagactc agcgaggagt taccgacatg cttaacgttt accgatgttc tcaggttgct   1380
tttcccggag agactatcat ggaggaggcc aagctctgta ctgagcgata cctgcgaaac   1440
gctctggaga acgccgacgc ctttgacaag tgggctatta agaagaacat tcgaggcgag   1500
gtggagtacg ctctcaagta cccctggcac cgatctatgc cccgactgga ggtgcgatct   1560
tacattggta actacggccc caacgatgtc tggcttggta agtcccttta catgatgccc   1620
tacatttcta acgagaagta ccttgagctt gccaagctgg acttcaactc tgtgcagtcc   1680
cttcaccagg aggagattcg agagcttgtc cgatggtgta agtcctctgg tttcactgag   1740
ctgaagttca cccgagatcg agttgttgag acttacttcg ctgttgcctc ctccatgttt   1800
gagcccgagt tctctacctg tcgagccgtt tacactaaga tttccgttct cctcgtcatt   1860
cttgacgacc tttacgatgg ctacggttct cccgacgaga tcaagctgtt ctccgaggct   1920
gtcaagcgat gggatctctc ccttcttgag cagatgcccg accacatgaa gatttgcttc   1980
ctgggtcttt acaacactgt taacgaggtt gctgaggagg gacgaaagac tcagggccac   2040
gatgttcttg gctacattcg aaacctttgg gagattcagc tcgccgcttt cacccgagag   2100
gctgagtggt cccagggcaa gtacgtgccc tctttcgatg agtacattga gaacgcccag   2160
gtttctattg gagttgctac tatcctcctt attactattc ttttcactga ggaggacgat   2220
attctctccc acattgatta cggttccaag tttctccgac tcgcttctct taccgctcga   2280
cttgccaacg acatcaagac ttaccaggag gagcgagccc acggcgaggt ggtttccgct   2340
attcagtgtt acatgaagga ccgacccgag attactgagg aggaggctct caagtacgtt   2400
tacggtcgaa tggttaacga tctcgccgag cttaactctg agtacctcaa gtctaacgag   2460
```

-continued atgccccaga actgcaagcg actggttttt gacactgccc gagttgccca gcttttcact 2520
atggagggtg acggcctcac ctactctgac actatggaga ttaaggagca catcaagaag 2580
tgcctctttg agcccgctac ctaa 2604

<210> SEQ ID NO 8
<211> LENGTH: 2379
<212> TYPE: DNA
<213> ORGANISM: Yarrowia lipolytica

<400> SEQUENCE: 8
atggttcttg gcctgcgatc taagatcatt ccccttcccg atcacaagct cggaaacatc 60
aagctcggtt ctgttaccaa cgctatttgc caccgaccct gtcgagtccg atgctctcac 120
tctactgctt cctctatgga ggaggctaag gagcgaatcc gagagacttt cggaaagatt 180
gagctttctc cctcctctta cgacactgct tgggttgcta tggtcccctc tcgatactct 240
atgaaccagc cctgttttcc ccagtgcctt gactggattc ttgagaacca gcgagaggac 300
ggttcttggg gcctcaaccc ctctcacccc cttctcgtta aggactccct ttcttccact 360
ctcgcttctc tccttgccct tcgaaagtgg cgaattggtg ataaccaggt ccagcgaggt 420
cttggcttta ttgagactca cggttgggct gtcgataaca aggatcagat ttctcccctt 480
ggttttgaga ttatctttcc ctgcatgatt aactacgctg agaagctcaa ccttgacctc 540
ccccttgacc ccaaccttgt taacatgatg ctctgcgagc gagagcttac cattgagcga 600
gccctcaaga acgagtttga gggtaacatg gctaacgttg agtactttgc tgagggactc 660
ggtgagcttt gtcactggaa ggagatgatg cttcgacagc gacacaacgg ctctctcttt 720
gactctcccg ccaccactgc cgctgccctt atttaccacc agtacgatga gaagtgcttt 780
ggctacctca actctatcct caagctccac gataactggg ttcccactat ttgccccact 840
aagattcact ctaacctttt cctcgttgat gcccttcaga acctcggagt tgaccgatac 900
tttaagactg aggttaagcg agttctcgat gagatttacc gactttggct tgagaagaac 960
gaggagattt tttctgacgt tgctcactgt gctatggctt ttcgactcct tcgaatgaac 1020
aactacgagg tttcctctga ggagcttgag ggttttgttg accaggagca cttctttact 1080
acctcctctg gcaagctcat gaaccacgtt gctattctgg agcttcaccg agcttctcag 1140
gtggctattc acgagcgaaa ggaccacatt cttgataaga tttctacttg gactcgaaac 1200
tttatggagc agaagctcct tgacaagcac attcccgacc gatctaagaa ggagatggag 1260
tttgctatgc gaaagtttta cggcactttc gaccgagtgg agactcgacg atacatcgag 1320
tcttacaaga tggactcctt taagattctc aaggccgctt accgatcttc cggtattaac 1380
aacattgacc ttctcaagtt ctctgagcac gatttcaacc tctgccagac ccgacacaag 1440
gaggagcttc agcagatgaa gcgatggttc accgattgca agctggagca ggtcggtctt 1500
tctcagcagt acctctacac ttcttacttc attatcgccg ctatcctctt tgagcccgag 1560
tacgctgatg ctcgacttgc ttacgctaag tacgccatca ttatcactgc cgtggacgat 1620
ttcttcgatt gttttatttg caaggaggag cttcagaaca tcatcgagct tgtcgagcga 1680
tgggagggat actctaccgt cggattccga tctgagcgag ttcgaatttt cttccttgcc 1740
ctttacaaga tggttgagga gattgctgcc aaggccgaga ctaagcaggg tcgatgtgtc 1800
aaggatcacc ttattaacct ttggattgat atgctcaagt gtatgctggt tgagcttgac 1860
ctttggaaga ttaagtccac taccccctct atcgaggagt acctttctgt tgcctgtgtt 1920
actattggtg ttccctgttt tgttctcact tctctctacc ttctcggacc caagctgtcc 1980

-continued

```
aaggacgtca ttgagtcctc tgaggtttcc gccctttgca actgtactgc cgctgtcgcc   2040

cgacttatta acgatattca ctcctacaag cgagagcagg ctgagtcctc tactaacatg   2100

gtttctatcc ttatcaccca gtcccagggt actatctctg aggaggaggc tattcgacag   2160

attaaggaga tgatggagtc taagcgacga gagcttctcg gaatggttct ccagaacaag   2220

gagtcccagc tcccccaggt gtgcaaggac ctcttttgga ctaccatcaa cgccgcttac   2280

tctattcaca ctcacggcga tggataccga ttccccgagg agttcaagaa ccacatcaac   2340

gatgttattt acaagcccct caaccagtac tccccctaa                         2379


<210> SEQ ID NO 9
<211> LENGTH: 14
<212> TYPE: DNA
<213> ORGANISM: Artificial sequence
<220> FEATURE:
<223> OTHER INFORMATION: artificially synthesized sequence with NheI
      restriction site

<400> SEQUENCE: 9

tgctagccac aaaa                                                       14
```

METHODS FOR PRODUCING ABIENOL

CROSS-REFERENCE TO RELATED APPLICATIONS

This application is the U.S. national phase of International Application No. PCT/US2015/063656 filed Dec. 3, 2015, which designated the U.S. and claims the benefit of U.S. Provisional Patent Application No. 62/089,511 filed Dec. 9, 2014, the entire contents of each of which are hereby incorporated by reference.

REFERENCE TO SEQUENCE LISTING SUBMITTED ELECTRONICALLY

The content of the electronically submitted sequence listing (Name: (4662_3413_AmendedSequenceListing_ST25.txt; Size: 41,574 bytes; and Date of Creation: Aug. 14, 2019) is herein incorporated by reference in its entirety.

FIELD OF THE INVENTION

Embodiments of the present disclosure relate to novel methods for the production of abienol and expression vectors and host cells useful in such methods.

BACKGROUND OF THE INVENTION

With a growing world economy and request for higher living standard, the demand for fragrance is on the rise. However, supplies of animal or plant based fragrance are limited, due to restraints in natural resources and animal protection. Attempts have been made to produce fragrances or their precursors from renewable sources such as microorganisms.

Ambergris is a prized, traditional fragrance ingredient that is a byproduct of the whale intestine. Ambrox, a substitute for ambergris, is produced by a chemical conversion of the diterpene sclareol, which is currently obtained from clary sage. Ambrox can also be generated from the related diterpene abienol, which has been found in fir and tobacco (Barrero et al. 1993, Tetrahedron 49:10405-10412). Also see FIG. 1.

The pathways to both abienol and sclareol in plants are proposed to involve two steps. The first step consists of the conversion of the isoprenoid pathway molecule geranylgeranyl diphosphate (GGPP) to a common intermediate named labda-13-en-8-ol diphosphate (LDPP) through the activity of a class II diterpene synthase (diTPS). The second step is catalyzed by a class I diTPS. There are several type of class I diTPS, each responsible for producing a specific end product. For example, abienol synthase (ABS) is for abienol production, and sclareol synthase (Scs) is responsible for sclareol production. See FIG. 2.

The enzymes involved in the two-step conversion of GGPP to sclareol or GGPP to abienol are plant specific and can be in the form of two independent enzymes or a single enzyme with two active sites. For example, in abienol production by tobacco (Sallaud et al. 2012, Plant J., 72(1): 1-17), the class II diTPS of tobacco (referred to as NtCPS2 by Sallaud et al., and referred to as Nt-class II-diTPS by the present disclosure) and the class I diTPS synthase of tobacco (referred to as abienol synthase of tobacco or Nt-ABS by the present disclosure), are in the form of two different protein molecules. Similarly, in sclareol production by clary sage (Schalk et al. 2012, Journal of Am. Chem Soc. 134:18900-18903); (Caniard et al. 2012, BMC Plant Biology 12:119), the class II diTPS of clary sage (referred to as Ss LPS by Schalk et al, and referred to as Ss-class II-diTPS by the present disclosure) and the class I diTPS synthase of clary sage (referred to as sclareol synthase of clary sage or Ss-Scs by the present disclosure), are also in the form of two independent protein molecules. In contrast, in the production of abienol by fir (Zerbe et al. 2012, J. Biol. Chem. 287: 12121-12131), both class I and class II diTPS subunits reside on one bifunctional class I/II abienol synthase (referred to as AbCAS by Zerbe et al. and by the present disclosure). Therefore in fir, GGPP is converted to abienol in the presence of the single bifunctional class VII abienol synthase. See FIG. 2.

Plant sources for sclareol and abienol are considered to be unreliable; thus a process for microbial production of either product could have commercial value. The class II diTPS and sclareol synthase genes from clary sage have been isolated and simultaneously expressed in *E. coli*, resulting in titers of approximately 1.5 grams per liter of sclareol in lab scale fermenters. Measurable production in *E. coli* of abienol has been achieved by the simultaneous expression of the class II diTPS and abienol synthase genes of tobacco, or the expression of the individual class VII abienol synthase of fir. However, production of abienol based on the existing methods is very low. It could therefore be desirable to produce abienol at a much higher titer.

SUMMARY OF THE INVENTION

We have now surprisingly found a novel method for significantly increasing the production rate of abienol from geranylgeranyl diphosphate (GGPP) in the presence of a combination of a class II diterpene synthase and a bifunctional class I/II abienol synthase. In one embodiment, the class II diTPS may be from tobacco or clary sage, and the bifunctional class I/II abienol synthase may be from fir. In another embodiment, the above class II diTPS may be a polypeptide comprising an amino acid sequence at least 50%, at least 60%, at least 70%, at least 80%, at least 90%, at least 95%, at least 97%, or at least 99% identical to SEQ ID NO:1. In another embodiment, the above class II diTPS may be a polypeptide comprising an amino acid sequence at least 50%, at least 60%, at least 70%, at least 80%, at least 90%, at least 95%, at least 97%, or at least 99% identical to SEQ ID NO:2. In another embodiment, the above bifunctional class I/II abienol synthase may be a polypeptide comprising an amino acid sequence at least 50%, at least 60%, at least 70%, at least 80%, at least 90%, at least 95%, at least 97%, or at least 99% identical to SEQ ID NO:3.

In another embodiment, the combination of the class II diTPS and the bifunctional class I/II abienol synthase is expressed by a recombinant host cell. In one embodiment, the recombinant cell is a genetically modified microorganism genetically modified to express at least one exogenous polypeptide selected from the group consisting of the above class II diTPS and the bifunctional class I/II abienol synthase. In one embodiment, the host cell comprises at least one nucleic acid encoding one or more of the amino acid sequences selected from the group consisting of said class II diTPS and said bifunctional class I/II abienol synthase.

In one embodiment, the recombinant host cell is a fungus. In another embodiment, the recombinant host cell is a *Yarrowia* fungus. In one specific embodiment, the recombinant host cell is *Yarrowia lipolytica*.

In another aspect of the disclosure, the present invention is directed to a recombinant host cell comprising a class II diterpene synthase and a bifunctional class I/II abienol synthase. In one embodiment, the class II diTPS may be from tobacco or clary sage, and the bifunctional class I/II abienol synthase may be from fir. In another embodiment, the above class II diTPS may be a polypeptide comprising an amino acid sequence at least 50%, at least 60%, at least 70%, at least 80%, at least 90%, at least 95%, at least 97%, or at least 99% identical to SEQ ID NO:1. In another embodiment, the above class II diTPS may be a polypeptide comprising an amino acid sequence at least 50%, at least 60%, at least 70%, at least 80%, at least 90%, at least 95%, at least 97%, or at least 99% identical to SEQ ID NO:2. In another embodiment, the above bifunctional class I/II abienol synthase may be a polypeptide comprising an amino acid sequence at least 50%, at least 60%, at least 70%, at least 80%, at least 90%, at least 95%, at least 97%, or at least 99% identical to SEQ ID NO:3.

In one embodiment, the recombinant host cell is a fungus. In another embodiment, the recombinant host cell is a *Yarrowia* fungus. In one specific embodiment, the recombinant host cell is *Yarrowia lipolytica.*

In another aspect of the disclosure, the present invention is directed to an expression vector comprising a polynucleotide molecule encoding an amino acid sequence comprising SEQ ID NO:1 and a polynucleotide molecule encoding an amino acid sequence comprising SEQ ID NO:3.

In another aspect of the disclosure, the present invention is directed to an expression vector comprising a polynucleotide molecule encoding an amino acid sequence comprising SEQ ID NO:2 and a polynucleotide molecule encoding an amino acid sequence comprising SEQ ID NO:3.

In one embodiment, one or both of the above described polynucleotide molecules are operationally linked to a transcriptional control sequence.

Overview of the Sequence Listing

The nucleic acid sequences listed in the accompanying sequence listing are shown using standard letter abbreviation for nucleotide bases. Only one strand of each nucleic acid sequence is shown, but the complementary strand is understood to be included by any reference to the displayed strand. In the accompanying sequence listing:

SEQ ID NO:1 is the amino acid sequence encoding the class II diterpene synthase from *Nicotiana tabacum*

```
MQVIITSSHRFFCHHLHQLKSPTSLSAQKAEFKKHGPRNWLFQTEGSLLY

KPVRLNCATSDASYLGNVNEYLESDHSKNSEEKDIQVSRTIQMKGLTEEI

KHMLNSMEDGRLNVLAYDTAWVSFIPNTTNNGNDQRPMFPSCLQWIIDNQ

LSDGSWGEEIVFCIYDRLLNTLVCVIALTLWNTCLHKRNKGVMFIKENLS

KLETGEVENMTSGFELVFPTLLEKAQQLDIDIPYDAPVLKDIYARREVKL

TRIPKDVIHTIPTTVLFSLEGLRDDLDWQRLLKLQMPDGSFLISPASTAF

AFMETNDEKCLAYLQNVVEKSNGGARQYPFDLVTRLWAIDRLQRLGISYY

FAEEFKELLNHVFRYWDEENGIFSGRNSNVSDVDDTCMAIRLLRLHGYDV

SPDALNNFKDGDQFVCFRGEVDGSPTHMFNLYRCSQVLFPGEKILEEAKN

FTYNFLQQCLANNRCLDKWVIAKDIPGEIWYALEFPWYASLPRVEARYYI

EQYGGADDIWIGKTLYRMPDVNNNVYLQAAKLDYNRCQSQHRFEWLIMQE

WFEKCNFQQFGISKKYLLVSYFLAAASIFEVEKSRERLAWAKSRIICKMI

TSYYNDEATTWTTRNSLLMEFKVSHDPTRKNGNETKEILVLKNLRQFLRQ
```

-continued

```
LSEETFEDLGKDIHHQLQNAWETWLVFLREEKNACQEETELLVRTINLSG

GYMTHDEILFDADYENLSNLTNKVCGKLNELQNDKVTGGSKNTNIELDMQ

ALVKLVFGNTSSNINQDIKQTFFAVVKTFYYSAHVSEEIMNFHISKVLFQ

QV
```

SEQ ID NO:2 is the amino acid sequence encoding the class II diterpene synthase from *Salvia sclarea*

```
MTSVNLSRAPAAIIRRRLQLQPEFHAECSWLKSSSKHAPFTLSCQIRPKQ

LSQIAELRVTSLDASQASEKDISLVQTPHKVEVNEKIEESIEYVQNLLMT

SGDGRISVSPYDTAVIALIKDLKGRDAPQFPSCLEWIAHHQLADGSWGDE

FFCIYDRILNTLACVVALKSWNLQSDIIEKGVTYIKENVHKLKGANVEHR

TAGFELVVPTFMQMATDLGIQGLPYDHPLIKEIADTKKQRLKEIPKDLVY

QMPTNLLYSLEGLGDLEWERLLKLQSGNGSFLTSPSSTAAVLMHTKDEKC

LKYIENALKNCDGGAPHTYPVDIFSRLWAIDRLQRLGISRFFQHEIKYFL

DHIESVWEETGVFSGRYTKFSDIDDTSMGVRLLKMHGYDVDPNVLKHFKQ

QDGKFSCYIGQSVESASPMYNLYRAAQLRFPGEEVFEEATKFAFNFLQEM

LVKDRLQERWVISDHLFDEIKLGLKMPWYATLPRVEAAYYLDHYAGSGDV

WIGKSFYRMPEISNDTYKELAILDFNRCQTQHQLEWIHMQEWYDRCSLSE

FGISKRELLRSYFLAAATIFEPERTQERLLLAKTRILSKMITSFVNISGT

TLSLDYNFNGLDEIISSANEDQGLAGTLLATFHQLLDGFDIYTLHQLKHV

WSQWFMKVQQGEGSGGEDAVLLANTLNICAGLNEDVLSNNEYTALSTLTN

KICNRLAQIQDNKILQVVDGSIKDKELEQDMQALVKLVLQENGGAVDRNI

RHTFLSVFKTFYYDAYHDDETTDLHIFKVL
```

SEQ ID NO:3 is the amino acid sequence encoding the bifunctional class I/II abienol synthase from *Abies balsamea*

```
MALPVYSLKSHIPITTIASAKMNYTPNKGMITANGRSRRIRLSPNKIVAC

AGEADRTFPSQSLEKTALFPDQFSEKNGTPSNFTPPNREFPPSFWNNDII

NSITASHKVQTGDRKRIQTLISEIKNVFNSMGDGETSPSAYDTAWVARIP

AVDGSEQPQFPQTLEWILQNQLKDGSWGEEFYFLAYDRLLATLACIITLT

IWRTGNVQLHKGIEFFRKQVVRMDDEADNHRPSGFEIVFPAMLNEAKSLG

LDLPYELPFIEQMVKKREAKLKMITTNVLYTIQTTLLYSLEGLHEIVDFD

KIIKLQSKDGSFLGSPASTAAVFMQTGNTKCLEFLEFVLRKFRNHVPSDY

PLDLFERLWVVDTVERLGIDRHFKKEIKDALDYVYSCWDERGIGWAKDSP

IADIDDTAMGLRILRLHGYNVSPDVLKTFKDENGEFFCFMGQTQRGVTDM

LNVYRCSQVAFPGETIMEEAKLCTERYLRNALENADAFDKWAIKKNIRGE

VEYALKYPWHRSMPRLEVRSYIGNYGPNDVWLGKSLYMMPYISNEKYLEL

AKLDFNSVQSLHQEEIRELVRWCKSSGFTELKFTRDRVVETYFAVASSMF

EPEFSTCRAVYTKISVLLVILDDLYDGYGSPDEIKLFSEAVKRWDLSLLE

QMPDHMKICFLGLYNTVNEVAEEGRKTQGHDVLGYIRNLWEIQLAAFTRE

AEWSQGKYVPSFDEYIENAQVSIGVATILLITILFTEEDDILSHIDYGSK

FLRLASLTARLANDIKTYQEERAHGEVVSAIQCYMKDRPEITEEEALKYV
```

-continued

YGRMVNDLAELNSEYLKSNEMPQNCKRLVFDTARVAQLFTMEGDGLTYSD

TMEIKEHIKKCLFEPAT

SEQ ID NO:4 is the amino acid sequence encoding the abienol synthase gene from *Nicotiana tabacum*

MVLGLRSKIIPLPDHKLGNIKLGSVTNAICHRPCRVRCSHSTASSMEEAK

ERIRETFGKIELSPSSYDTAWVAMVPSRYSMNQPCFPQCLDWILENQRED

GSWGLNPSHPLLVKDSLSSTLASLLALRKWRIGDNQVQRGLGFIETHGWA

VDNKDQISPLGFEIIFPCMINYAEKLNLDLPLDPNLVNMMLCERELTIER

ALKNEFEGNMANVEYFAEGLGELCHWKEMMLRQRHNGSLFDSPATTAAAL

IYHQYDEKCFGYLNSILKLHDNWVPTICPTKIHSNLFLVDALQNLGVDRY

FKTEVKRVLDEIYRLWLEKNEEIFSDVAHCAMAFRLLRMNNYEVSSEELE

GFVDQEHFFTTSSGKLMNHVAILELHRASQVAIHERKDHILDKISTWTRN

FMEQKLLDKHIPDRSKKEMEFAMRKFYGTFDRVETRRYIESYKMDSFKIL

KAAYRSSGINNIDLLKFSEHDFNLCQTRHKEELQQMKRWFTDCKLEQVGL

SQQYLYTSYFIIAAILFEPEYADARLAYAKYAIIITAVDDFFDCFICKEE

LQNIIELVERWEGYSTVGFRSERVRIFFLALYKMVEEIAAKAETKQGRCV

KDHLINLWIDMLKCMLVELDLWKIKSTTPSIEEYLSVACVTIGVPCFVLT

SLYLLGPKLSKDVIESSEVSALCNCTAAVARLINDIHSYKREQAESSTNM

VSILITQSQGTISEEEAIRQIKEMMESKRRELLGMVLQNKESQLPQVCKD

LFWTTINAAYSIHTHGDGYRFPEEFKNHINDVIYKPLNQYSP

SEQ ID NO:5 is the DNA sequence encoding the class II diterpene synthase from *Nicotiana tabacum*, as optimized for expression in *Yarrowia lipolytica* atgcaggttattattacctcctctcaccgatttttctgccaccaccttca ccagctcaagtcccctacctccctttctgctcagaaggctgagtttaaga agcacggcccccgaaactggcttttccagactgagggctctctcctttac aagcctgtccgactcaactgtgctacttctgatgcttcttaccttggtaa cgtgaacgagtaccttgagtctgaccactctaagaactccgaggagaagg atattcaggtttcccgaactatccagatgaagggtcttaccgaggagatc aagcacatgcttaactctatggaggacggacgacttaacgtcctcgccta cgacactgcttgggtttcctttattcctaacactaccaacaacggaaacg atcagcgacctatgtttccctcttgtcttcagtggattattgacaaccag ctttctgatggttcttggggagaggagattgttttctgcatttacgaccg actccttaacactctcgtttgtgttattgctctcactctctggaacactt gccttcacaagcgaaacaagggtgtgatgtttatcaaggagaacctttct aagctggagactggtgaggttgagaacatgacttctggttttgagcttgt ttttcccactctccttgagaaggcccagcagctcgatattgacattccct acgatgctcctgtcctgaaggatatttacgctcgacgagaggttaagctc acccgaatccctaaggacgttatccacactattcccactaccgttctctt ttctcttgagggactccgagatgacctcgactggcagcgactcctgaagc -continued tccagatgcctgacggttctttcctgatttcccctgcttccactgccttt gctttcatggagactaacgatgagaagtgtcttgcctaccttcagaacgt tgttgagaagtctaacggaggtgcccgacagtaccccttcgaccttgtta ctcgactttgggccattgatcgactccagcgactcggaatctcttactac tttgccgaggagttcaaggagcttctcaaccacgtgttccgatactggga cgaggagaacggaattttctctggacgaaactctaacgtttctgatgttg atgacacttgcatggctatccgacttctccgacttcacggttacgatgtt tcccctgacgcccttaacaacttcaaggacggcgaccagttcgtttgctt ccgaggtgaggtggacggttctcctacccacatgtttaacctctaccgat gttcccaggttcttttccccggagagaagattcttgaggaggctaagaac ttcacttacaacttccttcagcagtgccttgctaacaaccgatgcctcga caagtgggtcattgctaaggacatccccggcgagatttggtacgctcttg agtttccctggtacgcctcccttccccgagtggaggctcgatactacatt gagcagtacggcggagctgacgatatttggattggcaagactctctaccg aatgcccgatgtcaacaacaacgtttaccttcaggctgccaagctcgatt acaaccgatgccagtcccagcaccgatttgagtggctgattatgcaggag tggtttgagaagtgcaactttcagcagttcggaatttccaagaagtacct ccttgtttcttacttccttgctgccgcttctatttttgaggtcgagaagt cccgagagcgacttgcttgggctaagtctcgaattatctgtaagatgatt acttcttactacaacgatgaggccactacctggaccactcgaaactctct ccttatggagtttaaggtttctcacgaccctacccgaaagaacggtaacg agactaaggagatccttgttctcaagaaccttcgacagttccttcgacag ctttctgaggagactttcgaggaccttggcaaggacatccaccaccagct tcagaacgcttgggagacttggcttgttttccttcgagaggagaagaacg cttgtcaggaggagactgagcttctcgtgcgaactattaacctctctggc ggctacatgacccacgatgagattcttttcgatgccgactacgagaacct gtccaaccttaccaacaaggtttgtggcaagctcaacgagcttcagaacg acaaggtcactggcggctctaagaacaccaacattgagcttgacatgcag gctctcgttaagctggtttttggtaacacctcctctaacatcaaccagga cattaagcagactttctttgctgttgtcaagaccttctactactctgccc acgtttctgaggagattatgaactttcacatttccaaggtgctctttcag caggtctaa SEQ ID NO:6 is the DNA sequence the class II diterpene synthase from *Salvia sclarea*, as optimized for expression in *Yarrowia lipolytica* atgacttctgttaacctttcccgagcccccgctgccattatccgacgacg acttcagcttcagcctgagtttcacgccgagtgttcttggctgaagtctt cttccaagcacgccccttcaccctttcctgccagattcgacctaagcag ctctcccagattgccgagcttcgagttacttccctcgatgcttcccaggc ttccgagaaggacatttcccttgttcagactccccacaaggttgaggtta -continued acgagaagatcgaggagtctatcgagtacgtccagaaccttctcatgact tccggcgacggacgaatttctgtgtcccccctacgacaccgctgtgatcgc cctgattaaggacctcaagggtcgagatgcccctcagtttccctcttgtc ttgagtggattgcccaccaccagcttgctgatggctcttggggcgacgag ttcttctgtatttacgaccgaatcctgaacactctcgcttgtgtcgtcgc cctgaagtcttggaaccttcagtctgatattattgagaagggtgtgacct acatcaaggagaacgtccacaagctcaagggtgccaacgttgagcaccga actgccggattcgagcttgtggttcctacctttatgcagatggccactga ccttggcattcagggtcttccctacgatcacccccctcatcaaggagattg ctgacactaagaagcagcgactcaaggagattcccaaggatctcgtttac cagatgcctaccaaccttctctactcccttgagggactcggcgaccttga gtgggagcgactcctgaagctccagtccggcaacggctccttcctcactt ccccctcctccaccgccgccgtccttatgcacaccaaggacgagaagtgt ctgaagtacatcgagaacgccctcaagaactgcgacggaggtgctcccca cacttaccctgtcgatattttctctcgactttgggctattgatcgacttc agcgacttggtatttctcgattcttccagcacgagatcaagtacttcctc gatcacatcgagtccgtttgggaggagaccggagttttctctggacgata cactaagttttctgatattgatgacacctctatgggcgttcgacttctca agatgcacggatacgacgtcgatcccaacgttctcaagcacttcaagcag caggatggtaagttttcctgctacattggtcagtctgtcgagtctgcctc tcctatgtacaacctttaccgagccgcccagatcgattccctggtgagga ggtttttgaggaggccactaagtttgcctttaacttccttcaggagatgc ttgtcaaggatcgacttcaggagcgatgggtgatttccgaccaccttttc gatgagattaagctgggcctcaagatgccttggtacgccacccttccccg agtcgaggccgcttactacctcgatcactacgctggttctggtgatgttt ggattggcaagtctttctaccgaatgcctgagatttccaacgatacctac aaggagcttgccattctcgatttcaaccgatgccagactcagcaccagct tgagtggattcacatgcaggagtggtacgaccgatgctctctttccgagt tcggcatttccaagcgagagcttctccgatcttactttctcgccgccgct accattttcgagcctgagcgaactcaggagcgacttctccttgccaagac ccgaatcctgtctaagatgattacttcttttgtcaacatttccggtacta ccctttctctcgactacaacttcaacggcctcgatgagattatctcctct gccaacgaggatcagggtctggctggtactctcctggctaccttccacca gcttctcgacggattcgatatttacactctccaccagctcaagcacgttt ggtcccagtggttcatgaaggtgcagcagggagagggttctggcggcgag gacgccgtgctccttgccaacaccctcaacatctgcgccggcctcaacga ggacgtgctctccaacaacgagtacactgctctgtccaccctcaccaaca agatttgcaaccgactcgcccagatccaggacaacaagattctccaggtt gtggacggctccatcaaggataaggagcttgagcaggatatgcaggccct tgtcaagctcgtccttcaggagaacggcggagccgttgaccgaaacatcc gacacaccttcctttccgttttcaagactttctactacgatgcctaccac -continued gacgatgagactaccgaccttcacatcttcaaggttctctttcgacccgt tgtgtaa SEQ ID NO:7 is the DNA sequence encoding the bifunctional class I/II abienol synthase from *Abies balsamea*, as optimized for expression in *Yarrowia lipolytica* atggccctgcccgtttactctctcaagtcccacattcccatcactaccat cgcctctgctaagatgaactacacccccaacaagggtatgattaccgcca acggacgatctcgacgaatccgactttctcccaacaagatcgttgcttgt gctggtgaggctgatcgaactttcccctctcagtcccttgagaagaccgc tctctttcccgatcagttttctgagaagaacggtactccctctaacttca ctccccccaaccgagagtttccccctctttttggaacaacgatattatc aactctattactgcttctcacaaggttcagactggcgaccgaaagcgaat ccagactctcatttctgagattaagaacgtctttaactctatgggcgatg gtgagacttctccctctgcttacgacaccgcttgggttgctcgaatcccc gccgttgatggctctgagcagccccagtttccccagactcttgagtggat tcttcagaaccagctcaaggacggttcttggggtgaggagttctacttcc ttgcttacgaccgacttctcgctacccttgcctgcattattaccctcacc atttggcgaactggcaacgttcagcttcacaagggcattgagttcttccg aaagcaggttgttcgaatggacgatgaggctgataaccaccgaccctctg gttttgagattgtctttcccgctatgcttaacgaggctaagtcccttggt cttgacctgccctacgagcttcccttcattgagcagatggttaagaagcg agaggccaagctcaagatgattaccaccaacgtcctgtacaccattcaga ctaccctcctttactctctggagggccttcacgagattgttgacttcgat aagattatcaagctccagtccaaggacggttctttcctcggctcccccgc ttctactgccgctgttttcatgcagactggtaacactaagtgccttgagt tccttgagttcgttctccgaaagtttcgaaaccacgtgccctctgactac cccctcgatctctttgagcgactttgggtcgttgacactgttgagcgact tggcattgatcgacacttcaagaaggagatcaaggacgctcttgactacg tgtactcttgttgggacgagcgaggcattggctgggccaaggactctccc atcgccgatattgatgacactgctatgggccttcgaatccttcgactgca cggatacaacgtttcccccgatgttctcaagactttcaaggacgagaacg gagagttcttttgcttcatgggtcagactcagcgaggagttaccgacatg cttaacgtttaccgatgttctcaggttgcttttcccggagagactatcat ggaggaggccaagctctgtactgagcgatacctgcgaaacgctctggaga acgccgacgcctttgacaagtgggctattaagaagaacattcgaggcgag gtggagtacgctctcaagtacccctggcaccgatctatgccccgactgga ggtgcgatcttacattggtaactacggccccaacgatgtctggcttggta agtccctttacatgatgccctacatttctaacgagaagtaccttgagctt gccaagctggacttcaactctgtgcagtcccttcaccaggaggagattcg agagcttgtccgatggtgtaagtcctctggtttcactgagctgaagttca -continued

```
cccgagatcgagttgttgagacttacttcgctgttgcctcctccatgttt
gagcccgagttctctacctgtcgagccgtttacactaagatttccgttct
cctcgtcattcttgacgacctttacgatggctacggttctcccgacgaga
tcaagctgttctccgaggctgtcaagcgatgggatctctcccttcttgag
cagatgcccgaccacatgaagatttgcttcctgggtctttacaacactgt
taacgaggttgctgaggagggacgaaagactcagggccacgatgttcttg
gctacattcgaaacctttgggagattcagctcgccgctttcacccgagag
gctgagtggtcccagggcaagtacgtgccctctttcgatgagtacattga
gaacgcccaggtttctattggagttgctactatcctccttattactattc
ttttcactgaggaggacgatattctctcccacattgattacggttccaag
tttctccgactcgcttctcttaccgctcgacttgccaacgacatcaagac
ttaccaggaggagcgagcccacggcgaggtggtttccgctattcagtgtt
acatgaaggaccgacccgagattactgaggaggaggctctcaagtacgtt
tacggtcgaatggttaacgatctcgccgagcttaactctgagtacctcaa
gtctaacgagatgccccagaactgcaagcgactggtttttgacactgccc
gagttgcccagcttttcactatggagggtgacggcctcacctactctgac
actatggagattaaggagcacatcaagaagtgcctctttgagcccgctac
ctaa
```

SEQ ID NO:8 is the DNA sequence encoding the abienol synthase gene from *Nicotiana tabacum*, as optimized for expression in *Yarrowia lipolytica*

```
atggttcttggcctgcgatctaagatcattccccttcccgatcacaagct
cggaaacatcaagctcggttctgttaccaacgctatttgccaccgaccct
gtcgagtccgatgctctcactctactgcttcctctatggaggaggctaag
gagcgaatccgagagactttcggaaagattgagctttctccctcctctta
cgacactgcttgggttgctatggtccccctctcgatactctatgaaccagc
cctgttttccccagtgccttgactggattcttgagaaccagcgagaggac
ggttcttggggcctcaacccctctcaccccttctcgttaaggactccct
ttcttccactctcgcttctctccttgcccttcgaaagtggcgaattggtg
ataaccaggtccagcgaggtcttggctttattgagactcacggttgggct
gtcgataacaaggatcagatttctccccttggttttgagattatctttcc
ctgcatgattaactacgctgagaagctcaaccttgacctccccttgacc
ccaaccttgttaacatgatgctctgcgagcgagagcttaccattgagcga
gccctcaagaacgagtttgagggtaacatggctaacgttgagtactttgc
tgagggactcggtgagctttgtcactggaaggagatgatgcttcgacagc
gacacaacggctctctctttgactctcccgccaccactgccgctgccctt
atttaccaccagtacgatgagaagtgctttggctacctcaactctatcct
caagctccacgataactgggttcccactatttgccccactaagattcact
ctaacctttttcctcgttgatgcccttcagaacctcggagttgaccgatac
tttaagactgaggttaagcgagttctcgatgagatttaccgactttggct
tgagaagaacgaggagatttttctgacgttgctcactgtgctatggctt
ttcgactccttcgaatgaacaactacgaggtttcctctgaggagcttgag
ggttttgttgaccaggagcacttctttactacctcctctggcaagctcat
gaaccacgttgctattctggagcttcaccgagcttctcaggtggctattc
acgagcgaaaggaccacattcttgataagatttctacttggactcgaaac
tttatggagcagaagctccttgacaagcacattcccgaccgatctaagaa
ggagatggagtttgctatgcgaaagttttacggcactttcgaccgagtgg
agactcgacgatacatcgagtcttacaagatggactcctttaagattctc
aaggccgcttaccgatcttccggtattaacaacattgaccttctcaagtt
ctctgagcacgatttcaacctctgccagacccgacacaaggaggagcttc
agcagatgaagcgatggttcaccgattgcaagctggagcaggtcggtctt
tctcagcagtacctctacacttcttacttcattatcgccgctatcctctt
tgagcccgagtacgctgatgctcgacttgcttacgctaagtacgccatca
ttatcactgccgtggacgatttcttcgattgttttatttgcaaggaggag
cttcagaacatcatcgagcttgtcgagcgatgggagggatactctaccgt
cggattccgatctgagcgagttcgaattttcttccttgccctttacaaga
tggttgaggagattgctgccaaggccgagactaagcagggtcgatgtgtc
aaggatcaccttattaacctttggattgatatgctcaagtgtatgctggt
tgagcttgacctttggaagattaagtccactacccccctctatcgaggagt
acctttctgttgcctgtgttactattggtgttccctgttttgttctcact
tctctctaccttctcggacccaagctgtccaaggacgtcattgagtcctc
tgaggtttccgccctttgcaactgtactgccgctgtcgcccgacttatta
acgatattcactcctacaagcgagagcaggctgagtcctctactaacatg
gtttctatccttatcacccagtcccagggtactatctctgaggaggaggc
tattcgacagattaaggagatgatggagtctaagcgacgagagcttctcg
gaatggttctccagaacaaggagtcccagctcccccaggtgtgcaaggac
ctcttttggactaccatcaacgccgcttactctattcacactcacggcga
tggataccgattccccgaggagttcaagaaccacatcaacgatgttattt
acaagcccctcaaccagtactcccctaa
```

BRIEF DESCRIPTION OF THE DRAWINGS

Embodiments of the invention will now be shown, by way of example only, with reference to FIGS. 1-3 in which:

FIG. 3 shows a HPLC chromatogram of dodecane overlay of an abienol producing strain. A C18 column was utilized. Mobile phase was methanol ethanol 4:1, 0.1% TFA with an addition of 11% water during the first three minutes then straight methanol ethanol for 14 minutes. Samples were diluted 1:10 in mobile phase before injection.

DETAILED DESCRIPTION OF THE INVENTION

Figure 1:
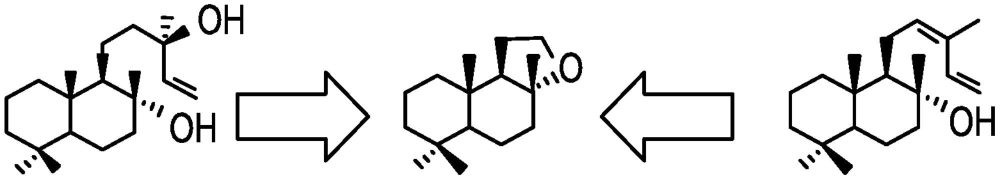
FIG. 1 shows that conversion of sclareol and abienol to Ambrox can be performed by a chemical process.
Figure 2A:
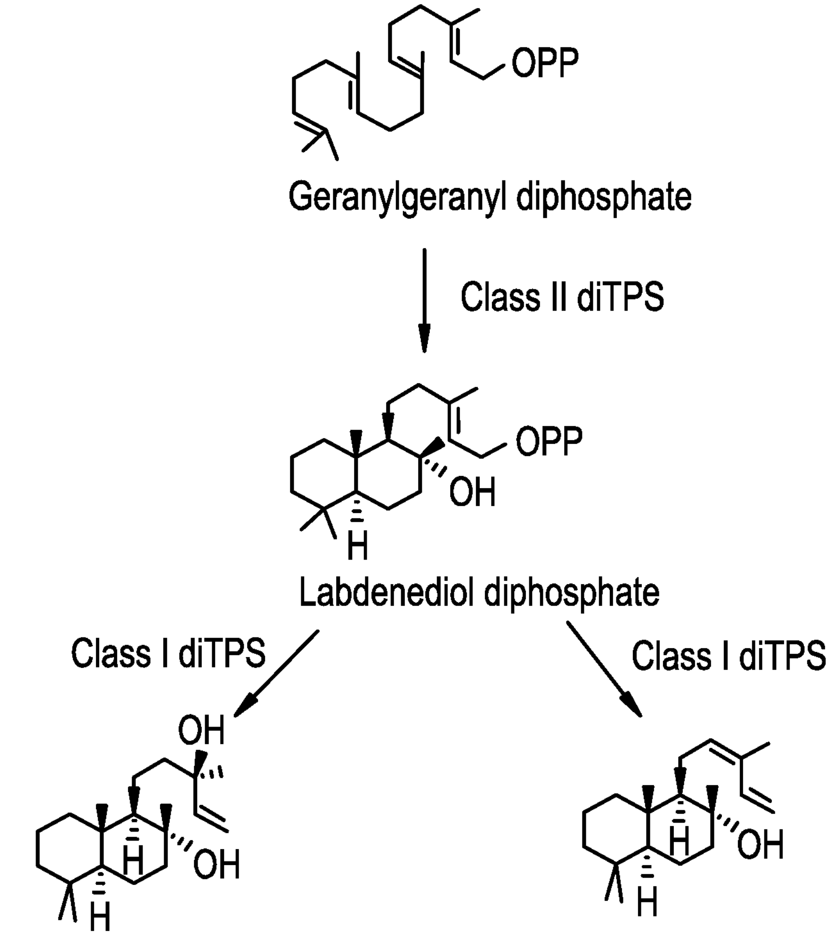
FIG. 2 shows the biochemical pathways to convert geranylgeranyl diphosphate to abienol in tobacco and to sclareol in clary sage. A. pathways to abienol in tobacco and sclareol in clary sage involve the activity of two separate enzymes: a type II diTPS that converts geranylgeranyl diphosphate (GGPP) to labda-13-en-8-01 diphosphate (LDPP) and a type I diTPS that converts LDPP to the final product. In tobacco, an abienol synthase (Nt-ABS) which is a type I diTPS converts LDPP to abienol. In clary sage, a sclareol synthase which is another type I diTPS converts LDPP to sclareol. B. in fir, the 2-step conversion of GGPP to LDPP and LDPP to abienol is performed by a single, bifunctional class I/II cis abienol synthase (Ab-CAS).
Figure 2B:
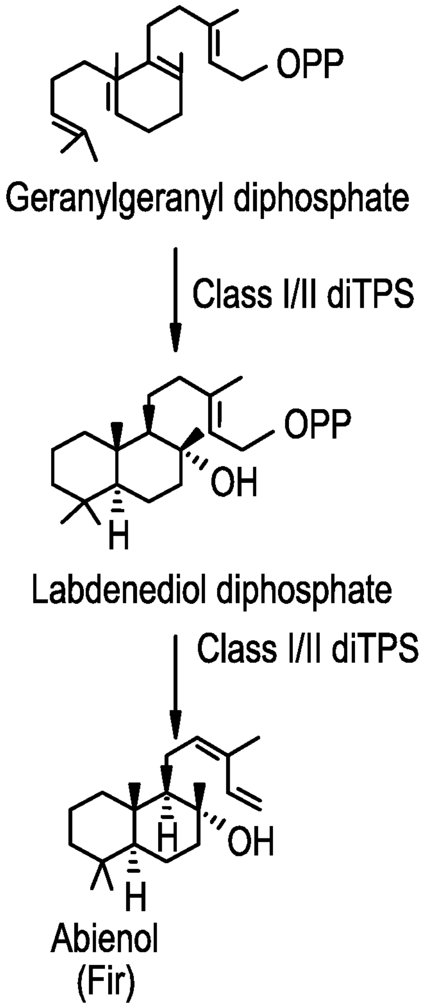

Unless otherwise defined herein, scientific and technical terms used herein will have the meanings that are commonly understood by those ordinary skilled in the art.

The term "class II diterpene synthase" or "class II diTPS" indicates an enzyme capable of catalyzing the conversion of geranylgeranyl diphosphate to labda-13-en-8-ol diphosphate. The class II diterpene synthase can be from various organisms, such as tobacco (*Nicotiana*) or clary sage (*Salvia*). Specific class II diterpene synthase utilized in the embodiments herein, derived from *Nicotiana tabacum* and *Salvia sclarea*, are referred to by an additional notation, e.g., "Nt-Class II-diTPS", and "Ss-Class II-diTPS", respectively. An example of a Nt-Class II-diTPS is the polypeptide having amino acid sequence SEQ ID NO:1. An example of a Ss-Class II-diTPS is the polypeptide having amino acid sequence SEQ ID NO:2

The term "class I diterpene synthase" or "class I diTPS" indicates an enzyme capable of catalyzing the conversion of labda-13-en-8-ol diphosphate to either abienol or sclareol. Specific class I diterpene synthase utilized in the embodiments herein, derived from *Nicotiana tabacum*, are referred to by an additional notation, e.g. "Nt-ABS", An example of a Nt-ABS is the polypeptide having amino acid sequence SEQ ID NO:4.

The term "bifunctional class I/II abienol synthase" or "bifunctional class I/II CAS" indicates an enzyme capable of catalyzing the conversion of geranylgeranyl diphosphate to abienol. The bifunctional class I/II abienol synthase has two active sites, having the function of a class I diterpene synthase and a class II diterpene synthase, respectively. Specific bifunctional class I/II abienol synthase utilized in particular embodiments herein, derived from *Abies balsamea*, are referred to by an additional notation, e.g., "Ab-bifunctional class I/II CAS" or simple, Ab-CAS. An example of Ab-bifunctional class I/II abienol synthase is the polypeptide having amino acid sequence SEQ ID NO:3.

Sequence Identity: The relatedness between two amino acid sequences or between two nucleotide sequences is described by the parameter "sequence identity".

For purposes of the present disclosure, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues}\times 100)/(\text{Length of Alignment}-\text{Total Number of Gaps in Alignment})$$

For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

$$(\text{Identical Deoxyribonucleotides}\times 100)/(\text{Length of Alignment}-\text{Total Number of Gaps in Alignment})$$

Nucleic acid construct: The term "nucleic acid construct" means a nucleic acid molecule, either single or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present disclosure.

Control sequences: The term "control sequences" means all components necessary for the expression of a polynucleotide encoding a polypeptide of the present disclosure. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present disclosure. The term "host cell" encompasses any progeny of a parent cell that is not identical to the parent cell due to mutations that occur during replication.

Variant: The term "variant" means a polypeptide having enzyme activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more amino acids adjacent to an amino acid occupying a position. In some embodiment, the above one or more amino acids are 1-3 amino acids.

In an embodiment of the method according to the first aspect of the invention, abienol is converted from geranylgeranyl diphosphate (GGPP) in the presence of a combination of class II diterpene synthase and bifunctional class I/II abienol synthase. The class II diterpene synthase according to embodiments herein may be from any organism that natively expresses an independent enzyme of class II diterpene synthase. In one embodiment, the class II diterpene synthase is from tobacco, or specifically, from *Nicotiana tabacum*. In another embodiment, the class II diterpene synthase is from clary sage, or specifically, from *Salvia sclarea*. The class II diterpene synthase according to embodiments herein may include, for example and without limitation, a polypeptide comprising an amino acid sequence having at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO:1 or SEQ ID NO:2.

The bifunctional class I/II abienol synthase according to embodiments herein may be from any organism which natively expresses a single enzyme with two active sites, having class I diterpene synthase activity and class II diterpene synthase activities, respectively. In one embodiment, the bifunctional class I/II abienol synthase is from fir, or specifically, from *Abies balsamea*. The bifunctional class I/II abienol synthase according to embodiments herein may include, for example and without limitation, a polypeptide comprising an amino acid sequence having at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO:3.

In an embodiment of the invention, the class II diTPS and the bifunctional class I/II abienol synthase are expressed by a recombinant host cell, such as a recombinant microorganism. Therefore, the steps of one aspect of the invention may take place within a host cell, i.e., the method may be at least partially an in vivo method. The host cell may be recombinant and may, for example, be a genetically modified microorganism. Therefore, a microorganism may be genetically modified, i.e., artificially altered from its natural state, to express both class II diTPS and bifunctional class I/II abienol synthase. In one embodiment, it expresses a combination of a Nt-Class II-diTPS and an Ab-bifunctional class I/II abienol synthase. In another embodiment, it expresses a combination of a Ss-Class II-diTPS and an Ab-bifunctional class I/II abienol synthase. Preferably, the enzymes are exogenous, i.e., not present in the cell prior to modification, having been introduced using microbiological methods such as are described herein. Furthermore, in the method of the invention, the enzymes may each be expressed by a recombinant host cell, either within the same host cell or in separate host cells. The abienol may be secreted from the host cell in which it is formed.

The host cell may be genetically modified by any manner known to be suitable for this purpose by the person skilled in the art. This includes the introduction of the genes of interest, such as one or more genes encoding the bifunctional class I/II abienol synthase and class II diTPS enzymes, into a plasmid or cosmid or other expression vector which are capable of reproducing within the host cell. Alternatively, the plasmid or cosmid DNA or part of the plasmid or cosmid DNA or a linear DNA sequence may integrate into the host genome, for example by homologous recombination or random integration. To carry out genetic modification, DNA can be introduced or transformed into cells by natural uptake or mediated by well-known processes such as electroporation. Genetic modification can involve expression of a gene under control of an introduced promoter. The introduced DNA may encode a protein which could act as an enzyme or could regulate the expression of further genes.

Such a host cell may comprise a nucleic acid sequence encoding a bifunctional class I/II abienol synthase and a class II diTPS. For example, the cell may comprise one nucleic acid sequence comprising SEQ ID NO. 3 and at least one nucleic acid sequence comprising SEQ ID NO:1 or SEQ ID NO:2, or a complement thereof, or a fragment of such a polynucleotide encoding a functional variant (which may be a fragment providing a functional variant) of any of the enzymes in bifunctional class I/II abienol synthase and class II diTPS, for example enzymes as described herein. The nucleic acid sequences encoding the enzymes may be exogenous, i.e., not naturally occurring in the host cell.

Therefore, another aspect of the invention provides a recombinant host cell, such as a microorganism, comprising a first polypeptide which is a class II diTPS, for example, having an amino acid sequence at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identical to SEQ ID NOs:1 or 2 and comprising a second polypeptide which is a bifunctional class I/II abienol synthase, for example, having an amino acid sequence at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identical to SEQ ID NO:3. The cell may also comprise polypeptides which are functional variants or fragments of any of the above sequences.

A suitable polynucleotide may be introduced into the cell by random integration, homologous recombination and/or may form part of an expression vector comprising a combination of polynucleotide sequences SEQ ID NOs:1 and 3, a combination of polynucleotide sequences SEQ ID NOs:1 and 2, or a complement thereof. Such an expression vector forms a another aspect of the invention. Suitable vectors for construction of such an expression vector are well known in the art and may be arranged to comprise the polynucleotide operably linked to one or more expression control sequences, so as to be useful to express the required enzymes in a host cell, for example a micro-organism as described above. For example, promoters including, but not limited to TEF1, HSP, and HYP promoters can be used in conjunction with endogenous genes and/or heterologous genes for modification of expression patterns of class II diTPS and a bifunctional class I/II abienol synthase. Similarly, exemplary terminator sequences include, but are not limited to, the use of *Yarrowia lipolytica* XPR2 terminator sequences.

In some embodiments, the recombinant or genetically modified host cell, as mentioned throughout this specification, may be any microorganism selected from the group consisting of yeast, fungi (such as members of the genus *Yarrowia*), protists, algae, bacteria, and archaea. The bacterium may comprise a gram-positive bacterium or a gram-negative bacterium including but not limited to the genera *Escherichia, Corynebacterium, Streptomyces, Bacillus, Pseudomonas, Paracoccus*, and *Rhodococcus*. In certain embodiments of the invention, yeast or fungi of genera including, but not limited to, *Aspergillus niger, Aspergillus terreus, Aspergillus nidulans, Aspergillus oryzae, Neurospora crassa, Blakeslea, Candida, Cryptococcus, Cunninghamella, Lipomyces, Mortierella, Mucor, Phycomyces, Pythium, Rhodosporidium, Rhodotorula, Trichosporon*, and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Escherichia coli, Fusarium sporotrichioides, F. graminearum, Fusarium venenatum, Gibberrella zea, G. fujikuroi, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutin is, R. gracilis, R. graminis, R. mucilaginosa, R. pinicola, Saccharomyces cerevisiae, Trichosporon pullans, T. cutaneum*, and *Yarrowia lipolytica* are used.

Particularly suitable microorganisms, for example, include *Yarrowia lipolytica, Escherichia coli, Fusarium venenatum, Gibberrella fujikuroi* and *Saccharomyces cerevisiae.*

The *Yarrowia* platform has been optimized for flux through the isoprenoid pathway and has achieved production levels of greater than 10 grams per liter of total carotenoids. Since diterpenes are also derived from the isoprenoid pathway, *Yarrowia* is well suited for high level production of abienol.

The recombinant host cell or microorganism may be used to express the enzymes mentioned above and a cell free extract then obtained by standard methods, for use in the method according to the first aspect of the invention.

Embodiments of the present disclosure also encompass variants of the polypeptides as defined herein. As used herein, a "variant" means a polypeptide in which the amino acid sequence differs from the base sequence from which it is derived in that one or more amino acids within the sequence are substituted for other amino acids. For example, a variant of SEQ ID NO:1 may have an amino acid sequence at least about 50% identical to SEQ ID NO:1, for example, at least about 55%, 60%, 65%, 70%, 75%, 80%, 85%, 90%, 91%, 92%, 93%, 94%, 95%, 96%, 97%, 98%, or 99% identical. The variants and/or fragments are functional variants/fragments in that the variant sequence has similar or identical functional enzyme activity characteristics to the enzyme having the non-variant amino acid sequence specified herein.

For example, a functional variant of SEQ ID NO:1 has similar or identical class II diTPS characteristics as SEQ ID NO:1. An example may be that the rate of conversion by a functional variant of SEQ ID NO: 1, of GGPP to LDPP, may be the same or similar, although said functional variant may also provide other benefits. For example, at least about 80%, 90%, 95%, 96%, 97%, 98%, 99% or at least about 100% the rate will be achieved when using the enzyme that is a functional variant of SEQ ID NO:1.

A functional variant or fragment of any of the above SEQ ID NO amino acid sequences, therefore, is any amino acid sequence which remains within the same enzyme category (i.e., has the same EC number). Methods of determining whether an enzyme falls within a particular category are well known to the skilled person, who can determine the enzyme category without use of inventive skill. Suitable methods may, for example, be obtained from the International Union of Biochemistry and Molecular Biology.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

Class Amino Acid Examples:
Nonpolar: A, V, L, I, P, M, F, W
Uncharged polar: G, S, T, C, Y, N, Q
Acidic: D, E
Basic: K, R, H.

The invention extends to a novel combination of class II diTPS and a bifunctional class I/II abienol synthase for converting GGPP to abienol. Significant enhancement of conversion rate from GGPP to abienol is the result of such novel combination. In a particular embodiment as shown in Example 3, a 10-fold enhancement in abienol titer was observed when the class II diTPS from either *Nicotiana tabacum* or *Salvia sclarea* was used in combination with a bifunctional class I/II abienol synthase from *Abies balsamea*, when comparing with that a bifunctional class I/II abienol synthase being used alone.

The above-described result is unexpected. It is conventionally recognized in the art that a single bifunctional enzyme would be more efficient in catalyzing a substrate than two separate enzymes which have the same two functions, due to a scaffolding effect (Zerbe et al. 2012, J. Biol. Chem. 287: pp 12121-12131). The reasoning is that expression of the two activities in the bifunctional enzyme is more balanced, and activities are maintained in close proximity to each other. This view is corroborated by the observation in this disclosure that a combination of class I and class II diTPS from *Nicotiana tabacum* produces little abienol compared to the class I/II bifunctional diTPS from *A. balsamea*. See Example 3.

Against the above teachings, the inventors of the present disclosure created transformants which contain a class II diTPS single function enzyme and a bifunctional class VII abienol synthase. The results showed that the titer of abienol production is significantly greater than that produced by the two-enzyme system of class I and class II diTPS, or by a single bifunctional class I/II abienol synthase. Adding a class II diTPS enzyme in addition to a bifunctional class I/II abienol synthase does not produces merely an additive effect. Instead, a synergistic effect is achieved, which is unexpected.

The following examples are intended to illustrate the invention without limiting its scope in any way.

EXAMPLES

Example 1

Construction of Vectors Containing the Class II diTPS Gene, the Bifunctional Class I/II Abienol Synthase Plasmids that were constructed and used in the present disclosure are shown in Table 1.

The bifunctional class I/II abienol synthase gene of *Abies balsamea* (Ab-CAS) was codon optimized according to *Yarrowia* codon bias, and synthesized de novo. During the de novo synthesis the sequence 5'-TGCTAGCCACAAAA (SEQ ID NO: 9), containing an NheI restriction site and a typical Kozak sequence for enabling efficient translation initiation, was added immediately upstream of the presumptive ATG start codon. The sequence ACGCGT-3', comprising an MluI restriction site, was added immediately downstream of the stop codon. This sequence was cleaved using NheI and MluI and ligated to pMB6655 cut with NheI and MluI to produce pMB6839. The resulting protein encoded by the Ab-CAS gene of pMB6839 is specified in SEQ ID No: 3. The class II diTPS gene of *Nicotinia tabacum* (Nt-Class II-diTPS) was cloned into expression vector pMB6674 as described above to create pMB6845. The protein sequence of Nt-Class II-diTPS gene encoded by pMB6845 is specified in SEQ ID No:2. The Ab-CAS gene and promoter and terminator in pMB6839 were excised by digestion with PvuII and SspI and cloned into the EcoRV site of pMB6845 to create pMB6847, which expresses both the Ab-CAS gene and the Nt-Class II-diTPS gene along with the hygromycin resistance gene HPH.

The abienol synthase gene of *Nicotinia tabacum* (Nt-ABS) was synthesized and cloned into pMB6655 as described for pMB6839, to create pMB6840. The protein sequence for the Nt-ABS gene of pMB6840 is specified in SEQ ID No:4. The Nt-ABS gene and promoter and terminator in pMB6840 was removed by digestion with PvuII and SspI, and cloned into the EcoRV site of pMB6845 to create pMB6849, which expresses both the Nt-ABS gene and the Nt-class II-diTPS gene along with the hygromycin resistance gene HPH.

The class II diTPS of *Salvia sclarea* (Ss-class II-diTPS) gene was synthesized and cloned into pMB6674 as described above to create pMB6874. The protein sequence of Ss-class II-diTPS is specified in SEQ ID No. 2. The Ab-CAS gene and expression signals of pMB6839 were excised by digestion with PvuII and SspI and cloned into the EcoRV site of pMB6874 to create pMB6879, which expresses both the Ab-ABS gene and Ss-class II-diTPSgene with hygromycin selection.

The gene sequences encoding amino acid sequences SEQ ID NOs 1-4 were codon optimized according to *Yarrowia* codon bias and the resulting nucleic acid sequences are SEQ ID NOs 5-8, respectively.

TABLE 1

| Plasmids | | | |
|---|---|---|---|
| Plasmid | Backbone | Insert (s) | Source |
| pMB6839 | pMB6655 (hygR) | Ab-CAS (class I/II) | Synthesized NheI-MluI fragment |
| pMB6845 | pMB6674 (hygR) | Nt-Class II-diTPS | Synthesized NheI-MluI fragment |
| pMB6847 | pMB6845 (hygR) | Ab-CAS (class I/II) + Nt-Class II-diTPS | Synthesized NheI-MluI fragment |
| pMB6840 | pMB6655 (hygR) | Nt-ABS (class I) | Synthesized NheI-MluI fragment |
| pMB6849 | pMB6845(hygR) | Nt-ABS(class I) + Nt-Class II-diTPS | Synthesized NheI-MluI fragment |
| pMB6874 | pMB6674 (hygR) | Ss-Class II-diTPS | Synthesized NheI-MluI fragment |

TABLE 1-continued

| Plasmids | | | |
|---|---|---|---|
| Plasmid | Backbone | Insert (s) | Source |
| pMB6879 | pMB6874 (hygR) | Ab-CAB (class I/II) + Ss-Class II-diTPS | Synthesized NheI-MluI fragment |

All basic molecular biology and DNA manipulation procedures described herein are generally performed according to Sambrook et al. or Ausubel et al. (J. Sambrook, E. F. Fritsch, T. Maniatis (eds). 1989. *Molecular Cloning: A Laboratory Manual*. Cold Spring Harbor Laboratory Press: New York; F. M. Ausubel, R. Brent, R. E. Kingston, D. D. Moore, J. G. Seidman, J. A. Smith, K. Struhl (eds.). 1998. *Current Protocols in Molecular Biology*. Wiley: New York).

Example 2

Construction of Recombinant Host Cells Containing Class II diTPS and Bifunctional Class I/II Abienol Synthase Genes In this example, the vectors containing class II diTPS and bifunctional class I/II abienol synthase genes were introduced into a host strain of *Y. lipolytica.*

The vectors described above were transformed into a *Y. lipolytica* strain (ML7206) which had previously been optimized for increased flux through the isoprenoid pathway. Host strain ML7206 is a prototrophic *Y. lipolytica* strain with the following genotype (MATB erg9-4789::ura3 {HMG-tr GGS carB}). Strain ML7206 was constructed by the introduction of heterologous genes under the control of constitutive promoters, coupled with several generations of cross-breeding, starting with MF350 and ATCC201249 as described in U.S. Pat. No. 7,851,199. The ERG9 gene, encoding squalene synthase, was replaced with a hypomorphic version harboring a point mutation (F317I) and an insertion of the URA3 gene (subsequently inactivated by mutation) directly after the stop codon.

The GGS gene and the truncated HMG gene ("HMG-tr") were derived from *Yarrowia* sequences corresponding to native geranylgeranyl pyrophosphate synthase and hydroxymethylglutaryl-CoA reductase genes, respectively. The carB gene was derived from *Mucor circinelloides*, and encodes a phytoene dehydrogenase activity, but has no bearing on the following example.

Example 3

Study of the Abienol Titer of the Recombinant Host Cells Containing a Class II diTPS Gene and a Bifunctional Class I/II CAS Gene In this example, the productions of abienol in recombinant host cells described in Example 2 were examined.

Figure 3A:
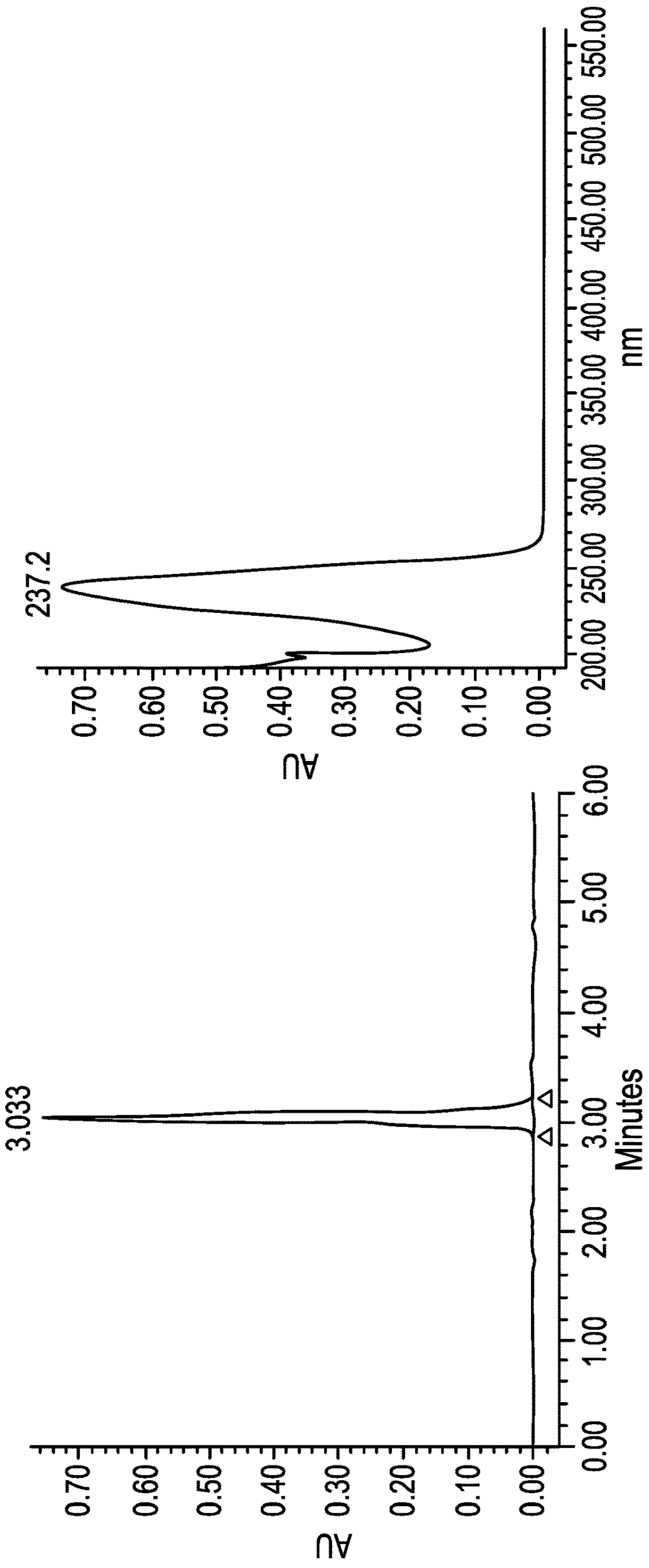
FIG. 3*a* shows the abienol peak of the commercial abeinol reference sample.
Figure 3B:
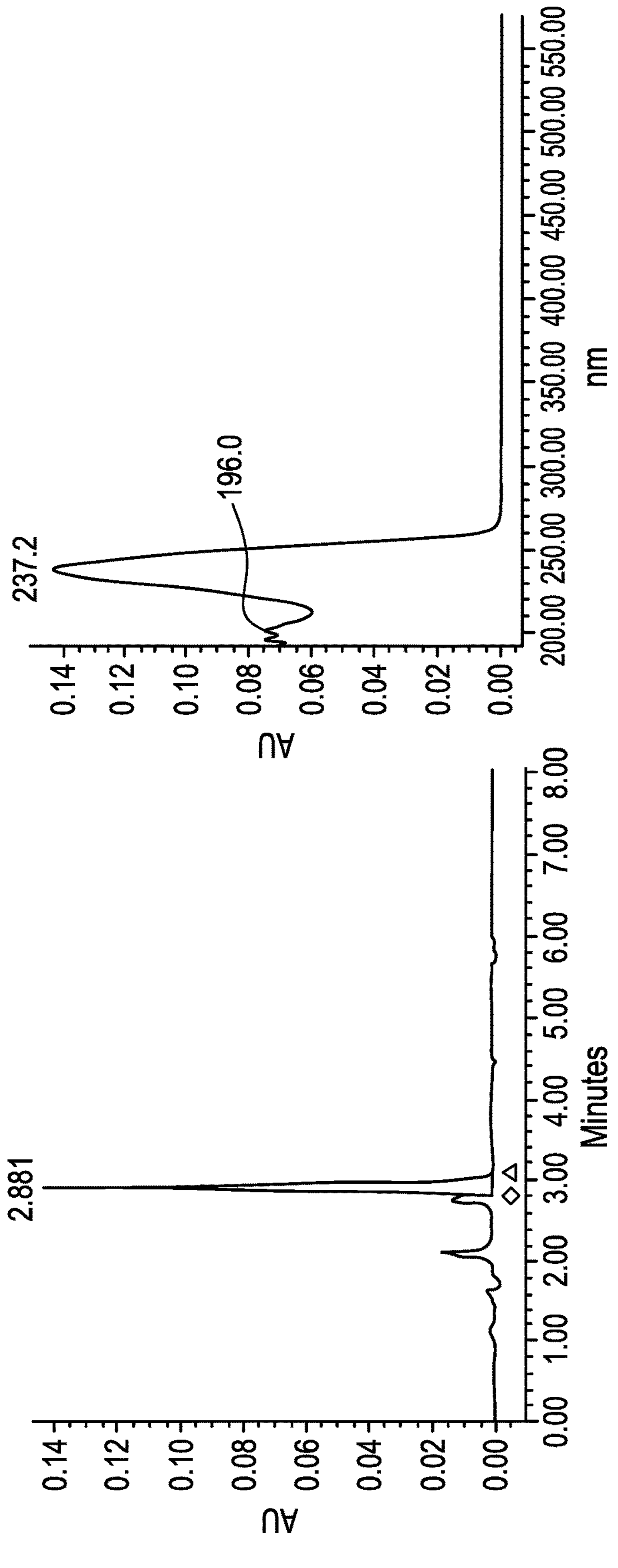
FIG. 3*b* shows the abienol peak of the abienol generated from the transformants.

The transformants described in Example 2 were grown in shake flasks on a rich medium (YPD) overlaid with a 10% volume of dodecane. Previous studies with isoprenoids have shown that the isoprenoid products are typically exported by microorganisms, and accumulate in a dodecane overlay. After growth at 28° C., 200 rpm, for 6 days, the dodecane fraction was removed from the shake flasks and analyzed by HPLC on a C18 column, with a photo-diode array detector. The HPLC set up consisted of a YMC PackPro C18 RS column [part # RS08503-1456WT 150×4.6 mm S3 μm] at a column temperature of 16° C., mobile phase consisted of a mixture of (400 mL Methanol, 100 mL Ethanol, and 0.1% Trifluoro-Acetic Acid) using an isocratic flow rate of 1 mL/min. The transformants containing the abienol synthase gene generated a peak at 2.90 minutes with an optimum absorbance of 237 nm (FIG. 3*b*). This peak was consistent with a reference abienol standard purchased from Toronto Research Chemicals Cat. #107600 (FIG. 3*a*).

TABLE 2

| Abienol production in transformants of isoprenoid optimized strain MB7206. | | | |
|---|---|---|---|
| Genes transformed into MB7206 | Abienol absorbance (millions), YP + 5% glucose | Abienol absorbance (millions), YP + 10% glucose | Abienol absorbance (millions), YP + 12.5% glucose |
| none | 0 | 0 | ND (Not done) |
| Tobacco Class I Nt ABS and Tobacco Class II Nt diTPS (plasmid pMB6849) | 0.4 | 0.4 | ND |
| Fir Bifunctional Class I/II Ab-CAS (plasmid pMB6839) | 1.9 | 2.3 | ND |
| Fir Bifunctional Class I/II Ab-CAS and tobacco Class II diTPS (plasmid pMB6847) | 18.5 | 23.8 | 22.5 |
| Fir Bifunctional Class I/II Ab-CAS and sage Class II diTPS (plasmid pMB6879) (4 clones tested) | ND | ND | 17.5 |

As shown in Table 2, transformation containing both Class II diTPS gene and Class I diTPS abienol synthase (ABS) gene from tobacco into *Yarrowia* resulted in very low production of abienol. Transformation of the bifunctional class I/II abienol synthase gene (Ab-CAS) of fir alone resulted in a slightly elevated production of abienol. Surprisingly, transformants which contain the fir bifunctional class I/II abienol synthase gene (Ab-CAS) together with either the tobacco class II di-TPS gene or the sage class II di-TPS gene produced significantly higher levels of abienol. This effect was repeatedly observed across three different medium compositions in the transformant containing the tobacco class II di-TPS gene and the Ab-CAS gene. It is unexpected to observe that the addition of the class II enzyme from either tobacco or sage could significantly surpass the activity of the bifunctional class I/II abienol synthase of fir alone, particularly given the fact that transformation of the Class II diTPS and Class I diTPS abienol synthase genes from tobacco resulted in very little product.

What is claimed is:

1. A method for producing abienol, which comprises converting geranylgeranyl diphosphate (GGPP) to abienol by contacting the GGPP with a combination of class II diterpene synthase (diTPS) and bifunctional class I/II abienol synthase (CAS) whereby the class II diTPS converts the GGPP to labdenediol diphosphate and the bifunctional CAS converts the GGPP to labdenediol diphosphate and the labdenediol diphosphate to abienol, wherein the class II diTPS comprises an amino acid sequence with at least 95% sequence identity to SEQ ID NO:1 or SEQ ID NO:2 and the bifunctional CAS comprises an amino acid sequence with at least 95% sequence identity to SEQ ID NO:3.

2. The method of claim 1, wherein the class II diTPS comprises the amino acid sequence of SEQ ID NO:1.

3. The method of claim 1, wherein the class II diTPS comprises the amino acid sequence of SEQ ID NO:2.

4. The method of claim 1, wherein the class II diTPS is from tobacco or clary sage.

5. The method of claim 1, wherein the bifunctional CAS comprises the amino acid sequence of SEQ ID NO:3.

6. The method of claim 1, wherein the bifunctional CAS is from fir.

7. The method of claim 1, wherein at least one of said class II diTPS and said bifunctional CAS is expressed by a recombinant host cell.

8. The method of claim 7, wherein the recombinant cell is a genetically modified microorganism genetically modified to express at least one exogenous polypeptide selected from the group consisting of said class II diTPS and said bifunctional CAS.

9. The method of claim 8, wherein the host cell comprises at least one nucleic acid encoding one or more of the amino acid sequences selected from the group consisting of said class II diTPS and said bifunctional CAS.

10. The method of claim 9, wherein the recombinant host cell is a fungus.

11. The method of claim 10, wherein the host cell is *Yarrowia lipolytica*.

* * * * *